(12) United States Patent
Bigioni et al.

(10) Patent No.: US 9,765,094 B2
(45) Date of Patent: Sep. 19, 2017

(54) ULTRASTABLE SILVER NANOPARTICLES

(71) Applicant: The University of Toledo, Toledo, OH (US)

(72) Inventors: Terry Bigioni, Toledo, OH (US); Anil Desireddy, Toledo, OH (US); Brian Conn, Toledo, OH (US)

(73) Assignee: The University of Toledo, Toledo, OH (US)

( * ) Notice: Subject to any disclaimer, the term of this patent is extended or adjusted under 35 U.S.C. 154(b) by 33 days.

(21) Appl. No.: 14/773,027

(22) PCT Filed: Mar. 14, 2014

(86) PCT No.: PCT/US2014/027707
§ 371 (c)(1),
(2) Date: Sep. 4, 2015

(87) PCT Pub. No.: WO2014/152764
PCT Pub. Date: Sep. 25, 2014

(65) Prior Publication Data
US 2016/0009736 A1  Jan. 14, 2016

Related U.S. Application Data

(60) Provisional application No. 61/789,443, filed on Mar. 15, 2013, provisional application No. 61/867,912, filed on Aug. 20, 2013.

(51) Int. Cl.
| | | |
|---|---|---|
| *C07F 1/00* | (2006.01) |
| *A61K 8/02* | (2006.01) |
| *B82B 1/00* | (2006.01) |
| *A61K 33/38* | (2006.01) |
| *B22F 1/00* | (2006.01) |
| *B22F 9/24* | (2006.01) |
| *A61K 8/46* | (2006.01) |
| *A61Q 19/00* | (2006.01) |
| *A61K 8/19* | (2006.01) |
| *A61K 8/58* | (2006.01) |
| *A61K 47/48* | (2006.01) |

(Continued)

(52) U.S. Cl.
CPC .................. *C07F 1/00* (2013.01); *A61K 8/19* (2013.01); *A61K 8/46* (2013.01); *A61K 8/58* (2013.01); *A61K 33/38* (2013.01); *A61K 47/48023* (2013.01); *A61K 49/0052* (2013.01); *A61Q 19/00* (2013.01); *B22F 1/0018* (2013.01); *B22F 1/0062* (2013.01); *B22F 9/24* (2013.01); *B82B 1/00* (2013.01); *C07F 9/5045* (2013.01); *C07H 23/00* (2013.01); *H01G 9/2059* (2013.01); *A61K 2800/10* (2013.01); *A61K 2800/58* (2013.01); *A61K 2800/652* (2013.01)

(58) Field of Classification Search
CPC ..... C07F 1/00; A61K 8/19; A61K 8/46; B22F 1/0018; B22F 1/0062
USPC ........... 556/21, 113; 546/6; 536/121; 75/371
See application file for complete search history.

(56) References Cited

PUBLICATIONS

Yang et al., Nature Communications, DOI: 10.1038/ncomms3422, (2013).*

(Continued)

*Primary Examiner* — Porfirio Nazario Gonzalez
(74) *Attorney, Agent, or Firm* — MacMillan, Sobanski & Todd, LLC

(57) ABSTRACT

Ultrastable silver nanoparticles, methods of making the same, and methods of using the same, are disclosed.

20 Claims, 40 Drawing Sheets
(19 of 40 Drawing Sheet(s) Filed in Color)

(51) Int. Cl.
*A61K 49/00* (2006.01)
*C07F 9/50* (2006.01)
*C07H 23/00* (2006.01)
*H01G 9/20* (2006.01)

(56) References Cited

PUBLICATIONS

Chakraborty et al., The Journal of Physical Letters, vol. 4, pp. 3351-3355 (2013).*

* cited by examiner

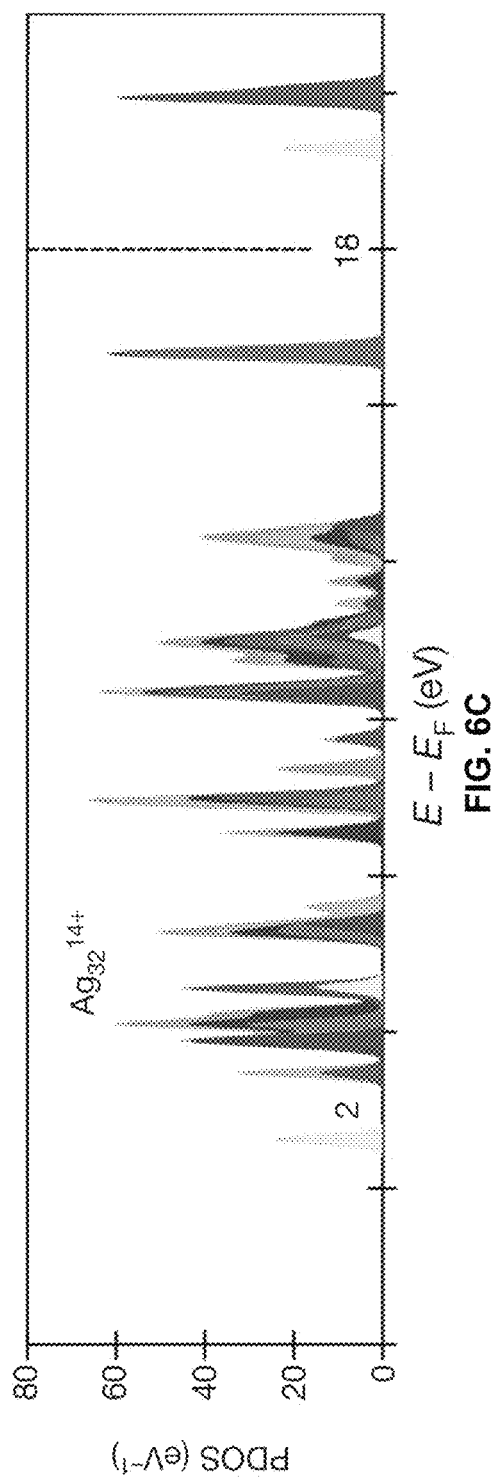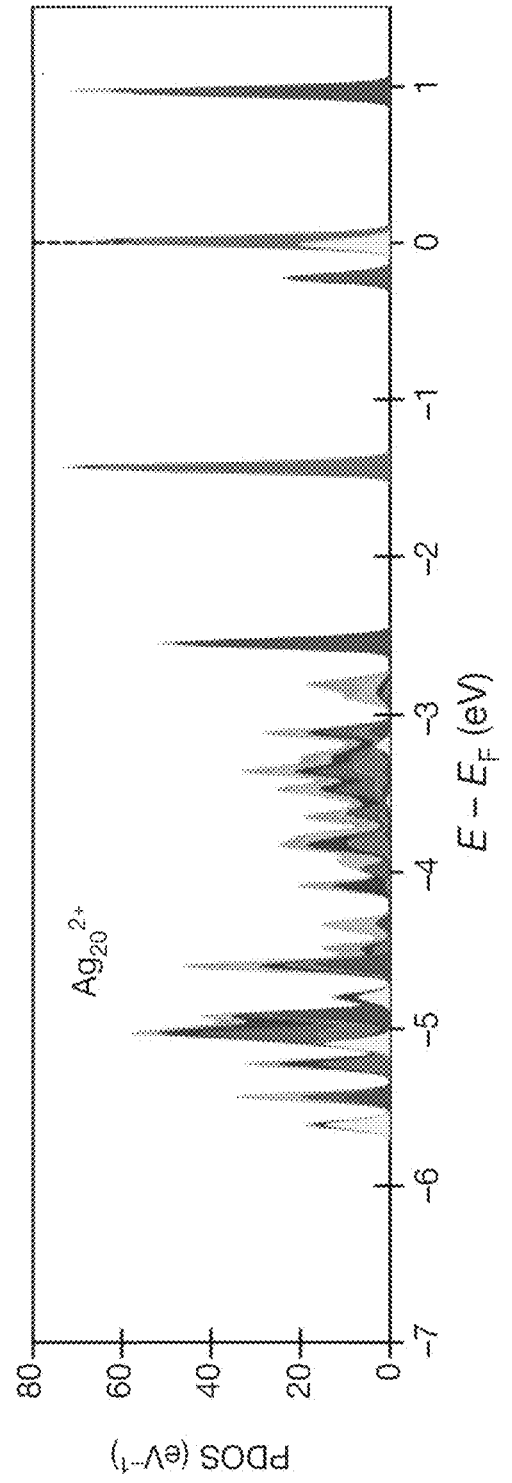

Table 3 – Sample and Crystal Data

| | | |
|---|---|---|
| Chemical formula | $C_{210}H_{150}Ag_{44}Na_4O_{60}S_{30}$ | |
| Formula weight | 9433.34 – not including the solvent | |
| Temperature | 150(2) K | |
| Wavelength | 1.54178 Å | |
| Crystal system | trigonal | |
| Space group | R -3 c | |
| Unit cell dimensions | a = 25.7611(3) Å | $\alpha = 90°$ |
| | b = 25.7611(3) Å | $\beta = 90°$ |
| | c = 124.434(3) Å | $\gamma = 120°$ |
| Volume | 71515.2(19) Å$^3$ | |
| Z | 6 | |
| Density (calculated) | 1.314 g/cm$^3$ – not including the solvent | |
| Absorption coefficient | 15.703 mm$^{-1}$ – not including the solvent | |
| F(000) | 26892 - – not including the solvent | |

FIG. 12

Table 4 – Data Collection and Structure Refinement

| | |
|---|---|
| Theta range for data collection | 2.10 to 68.10° |
| Index ranges | -28<=h<=29, -29<=k<=28, -120<=l<=145 |
| Reflections collected | 140794 |
| Independent reflections | 14088 [R(int) = 0.0611] |
| Structure solution technique | direct methods |
| Structure solution program | SHELXS-97 (Sheldrick, 2008) |
| Refinement method | Full-matrix least-squares on $F^2$ |
| Refinement program | SHELXL-97 (Sheldrick, 2008) |
| Function minimized | $\Sigma\, w(F_o^2 - F_c^2)^2$ |
| Data / restraints / parameters | 14088 / 11 / 471 |
| Goodness-of-fit on $F^2$ | 1.136 |
| $\Delta/\sigma_{max}$ | 0.007 |
| Final R indices | 10518 data; I>2σ(I)  R1 = 0.0520, wR2 = 0.1648 |
| | all data  R1 = 0.0790, wR2 = 0.1834 |
| Weighting scheme | $w=1/[\sigma^2(F_o^2)+(0.0924P)^2+1300.4352P]$ where $P=(F_o^2+2F_c^2)/3$ |
| Largest diff. peak and hole | 1.028 and -1.974 eÅ$^{-3}$ |
| R.M.S. deviation from mean | 0.250 eÅ$^{-3}$ |

FIG. 13

Table 5 – Atomic Coordinates and Equivalent Isotropic Atomic Displacement Parameters

|      | x/a         | y/b         | z/c         | U(eq)       |
|------|-------------|-------------|-------------|-------------|
| Ag1  | 0.95060(2)  | 0.02170(3)  | 0.982756(4) | 0.02507(15) |
| Ag2  | 0.88502(3)  | 0.91937(3)  | 0.995879(4) | 0.02579(15) |
| Ag3  | 0.88101(3)  | 0.81345(3)  | 0.987908(5) | 0.03308(17) |
| Ag4  | 0.0         | 0.0         | 0.963847(8) | 0.0329(3)   |
| Ag5  | 0.87181(3)  | 0.91059(3)  | 0.972963(5) | 0.03961(19) |
| Ag6  | 0.83063(3)  | 0.98404(3)  | 0.987962(5) | 0.03928(18) |
| Ag7  | 0.80590(4)  | 0.97293(4)  | 0.96307(6)  | 0.0557(2)   |
| Ag8  | 0.73718(4)  | 0.86516(4)  | 0.977099(7) | 0.0564(2)   |
| S1   | 0.78881(12) | 0.80444(12) | 0.97710(2)  | 0.0501(6)   |
| S2   | 0.89503(12) | 0.97228(13) | 0.95560(2)  | 0.0487(6)   |
| S3   | 0.83900(12) | 0.06362(12) | 0.97498(2)  | 0.0487(6)   |
| S4   | 0.73744(11) | 0.89700(13) | 0.99627(2)  | 0.0484(6)   |
| S5   | 0.69638(15) | 0.90523(18) | 0.96328(3)  | 0.0785(10)  |
| C11  | 0.7712(6)   | 0.7589(5)   | 0.96557(9)  | 0.058(3)    |
| C12A | 0.8145(12)  | 0.7748(12)  | 0.9573(2)   | 0.072(7)    |
| C13A | 0.8008(16)  | 0.7383(17)  | 0.9479(3)   | 0.101(10)   |
| C15A | 0.7006(13)  | 0.6687(13)  | 0.9566(2)   | 0.074(7)    |
| C16A | 0.7182(13)  | 0.7070(13)  | 0.9654(2)   | 0.076(7)    |
| C17A | 0.7313(18)  | 0.6513(17)  | 0.9371(2)   | 0.087(10)   |
| O11A | 0.7661(13)  | 0.6626(13)  | 0.9305(2)   | 0.133(9)    |
| O12A | 0.6758(13)  | 0.5941(13)  | 0.9395(2)   | 0.117(8)    |
| C14  | 0.7384(8)   | 0.6810(8)   | 0.94822(13) | 0.094(5)    |
| C12B | 0.7187(17)  | 0.7449(17)  | 0.9598(3)   | 0.104(11)   |
| C13B | 0.7003(19)  | 0.7058(19)  | 0.9507(3)   | 0.123(13)   |
| C15B | 0.7789(14)  | 0.6863(14)  | 0.9543(2)   | 0.080(8)    |
| C16B | 0.7958(13)  | 0.7252(13)  | 0.9635(2)   | 0.073(7)    |
| C17B | 0.7146(18)  | 0.6280(15)  | 0.9402(3)   | 0.084(10)   |
| O11B | 0.7472(11)  | 0.6142(11)  | 0.93641(19) | 0.104(7)    |
| O12B | 0.6723(15)  | 0.6316(15)  | 0.9335(3)   | 0.156(11)   |
| C21  | 0.8721(5)   | 0.9222(6)   | 0.94444(9)  | 0.061(3)    |
| C24  | 0.8322(8)   | 0.8442(8)   | 0.92712(12) | 0.097(5)    |

FIG. 14

| | | | | |
|---|---|---|---|---|
| C22A | 0.8122(18) | 0.8979(17) | 0.9409(3) | 0.111(11) |
| C23A | 0.7893(19) | 0.8561(19) | 0.9322(3) | 0.121(13) |
| C25A | 0.8867(14) | 0.8706(14) | 0.9303(2) | 0.081(8) |
| C26A | 0.9085(14) | 0.9108(14) | 0.9390(3) | 0.085(8) |
| C27A | 0.816(3) | 0.820(3) | 0.9161(3) | 0.17(3) |
| O21A | 0.7503(16) | 0.7774(16) | 0.9160(3) | 0.163(12) |
| O22A | 0.8421(11) | 0.7942(11) | 0.9131(2) | 0.108(7) |
| C22B | 0.8698(14) | 0.8632(14) | 0.9457(3) | 0.084(8) |
| C23B | 0.8530(15) | 0.8228(15) | 0.9374(3) | 0.088(9) |
| C25B | 0.8368(15) | 0.8927(16) | 0.9266(3) | 0.088(9) |
| C26B | 0.8577(13) | 0.9356(13) | 0.9352(2) | 0.076(7) |
| C27B | 0.8073(12) | 0.7963(12) | 0.91900(19) | 0.055(6) |
| O22B | 0.8077(13) | 0.7474(13) | 0.9196(2) | 0.133(9) |
| O21B | 0.7912(14) | 0.8160(14) | 0.9097(2) | 0.128(9) |
| C31 | 0.7745(6) | 0.0673(6) | 0.97858(10) | 0.071(4) |
| C32A | 0.7268(13) | 0.0498(9) | 0.9711(2) | 0.067(7) |
| C33A | 0.6757(14) | 0.0483(11) | 0.9739(3) | 0.078(8) |
| C34A | 0.668(3) | 0.0607(18) | 0.9834(4) | 0.12(2) |
| C35A | 0.7133(15) | 0.0808(13) | 0.9914(3) | 0.082(6) |
| C36A | 0.7663(14) | 0.0824(12) | 0.9885(3) | 0.076(6) |
| O31A | 0.5720(11) | 0.0459(12) | 0.9805(2) | 0.103(7) |
| O32A | 0.5866(17) | 0.0403(18) | 0.9993(3) | 0.167(13) |
| C37A | 0.6103(17) | 0.0573(18) | 0.9881(3) | 0.099(8) |
| C32B | 0.7455(15) | 0.0791(10) | 0.9705(3) | 0.095(10) |
| C33B | 0.6918(15) | 0.0822(13) | 0.9733(3) | 0.095(10) |
| C34B | 0.674(2) | 0.0756(15) | 0.9849(2) | 0.088(14) |
| C35B | 0.7021(14) | 0.0564(13) | 0.9937(3) | 0.082(6) |
| C36B | 0.7533(14) | 0.0563(12) | 0.9907(3) | 0.076(6) |
| C37B | 0.6270(17) | 0.0938(17) | 0.9871(3) | 0.099(8) |
| O32B | 0.6086(10) | 0.0791(10) | 0.99677(18) | 0.087(6) |
| O31B | 0.5925(15) | 0.0862(15) | 0.9792(3) | 0.139(10) |

FIG. 14 cont.

| | | | | |
|---|---|---|---|---|
| C41A | 0.6823(12) | 0.9210(13) | 0.9984(2) | 0.046(7) |
| C42A | 0.6687(14) | 0.9313(15) | 0.0082(2) | 0.072(8) |
| C43A | 0.6213(16) | 0.9432(17) | 0.0102(3) | 0.093(10) |
| C44A | 0.5909(19) | 0.951(2) | 0.0018(4) | 0.139(16) |
| C45A | 0.6004(14) | 0.9319(15) | 0.9921(3) | 0.075(8) |
| C46A | 0.6478(12) | 0.9224(13) | 0.9899(2) | 0.059(7) |
| C47A | 0.5377(19) | 0.960(2) | 0.0048(4) | 0.118(13) |
| O41A | 0.5279(12) | 0.9598(13) | 0.0143(2) | 0.107(7) |
| O42A | 0.5026(13) | 0.9461(13) | 0.9971(2) | 0.121(6) |
| C41B | 0.6735(11) | 0.9010(12) | 0.99882(18) | 0.038(6) |
| C42B | 0.6588(13) | 0.9036(14) | 0.0097(2) | 0.066(7) |
| C43B | 0.6093(14) | 0.9118(15) | 0.0120(2) | 0.077(8) |
| C44B | 0.5770(9) | 0.9166(10) | 0.00319(18) | 0.047(5) |
| C45B | 0.5836(15) | 0.9016(16) | 0.9935(3) | 0.083(9) |
| C46B | 0.6348(15) | 0.8962(16) | 0.9911(3) | 0.078(9) |
| C47B | 0.5210(11) | 0.9196(13) | 0.0062(2) | 0.062(6) |
| O41B | 0.5079(13) | 0.9195(14) | 0.0156(2) | 0.120(9) |
| O42B | 0.4849(13) | 0.9095(13) | 0.9990(2) | 0.121(6) |
| C51 | 0.6733(7) | 0.8548(7) | 0.95310(13) | 0.086(4) |
| C54 | 0.6307(10) | 0.7706(10) | 0.93609(16) | 0.127(7) |
| C52A | 0.6703(16) | 0.7982(18) | 0.9542(3) | 0.115(12) |
| C53A | 0.6498(19) | 0.754(2) | 0.9454(4) | 0.139(15) |
| C55A | 0.6375(17) | 0.8305(19) | 0.9344(3) | 0.121(13) |
| C56A | 0.6576(14) | 0.8724(15) | 0.9429(3) | 0.091(9) |
| O51A | 0.6157(19) | 0.6805(19) | 0.9283(3) | 0.194(15) |
| O52A | 0.5975(14) | 0.7419(14) | 0.9178(3) | 0.141(10) |
| C52B | 0.7101(19) | 0.8657(19) | 0.9435(3) | 0.119(12) |
| C53B | 0.691(2) | 0.821(2) | 0.9350(4) | 0.126(13) |
| C55B | 0.592(2) | 0.7550(19) | 0.9458(4) | 0.124(13) |
| C56B | 0.6165(18) | 0.8017(18) | 0.9543(3) | 0.112(11) |
| O51B | 0.6462(18) | 0.7389(16) | 0.9195(3) | 0.174(13) |
| O52B | 0.5565(16) | 0.6709(15) | 0.9299(2) | 0.149(11) |
| C57 | 0.6050(12) | 0.7235(13) | 0.9273(2) | 0.146(8) |

FIG. 14 cont.

Table 6 – Bond Lengths (Å) for $Ag_{44}$

| | | | |
|---|---|---|---|
| Ag1-Ag2#4 | 2.8126(8) | Ag1-Ag6 | 2.8130(9) |
| Ag1-Ag1#4 | 2.8162(10) | Ag1-Ag1#3 | 2.8163(10) |
| Ag1-Ag5#4 | 2.8177(9) | Ag1-Ag5 | 2.8262(9) |
| Ag1-Ag2 | 2.8314(8) | Ag1-Ag2#1 | 2.8430(8) |
| Ag1-Ag3#4 | 2.8430(8) | Ag1-Ag4 | 2.8600(10) |
| Ag2-Ag1#3 | 2.8126(8) | Ag2-Ag6#2 | 2.8259(9) |
| Ag2-Ag2#1 | 2.8261(7) | Ag2-Ag2#2 | 2.8262(7) |
| Ag2-Ag6 | 2.8361(9) | Ag2-Ag1#2 | 2.8430(8) |
| Ag2-Ag3 | 2.8561(8) | Ag2-Ag3#1 | 2.8645(8) |
| Ag2-Ag5 | 2.8673(9) | Ag3-S4#2 | 2.599(3) |
| Ag3-S1 | 2.637(3) | Ag3-S3#3 | 2.642(3) |
| Ag3-Ag1#3 | 2.8431(8) | Ag3-Ag2#2 | 2.8643(8) |
| Ag3-Ag6#3 | 3.1379(10) | Ag3-Ag5 | 3.2203(10) |
| Ag3-Ag6#2 | 3.2235(9) | Ag4-S2#4 | 2.635(3) |
| Ag4-S2#3 | 2.635(2) | Ag4-S2 | 2.635(3) |
| Ag4-Ag1#4 | 2.8602(10) | Ag4-Ag1#3 | 2.8602(10) |
| Ag4-Ag5#4 | 3.1449(8) | Ag4-Ag5#3 | 3.1449(8) |
| Ag4-Ag5 | 3.1449(8) | Ag5-S1 | 2.543(3) |
| Ag5-S2 | 2.569(3) | Ag5-Ag1#3 | 2.8178(9) |
| Ag5-Ag8 | 3.0992(10) | Ag5-Ag7 | 3.1152(10) |
| Ag5-Ag6 | 3.1930(9) | Ag6-S3 | 2.533(3) |
| Ag6-S4 | 2.545(3) | Ag6-Ag2#1 | 2.8257(9) |
| Ag6-Ag8 | 3.1030(11) | Ag6-Ag3#4 | 3.1380(10) |
| Ag6-Ag7 | 3.1464(10) | Ag6-Ag3#1 | 3.2234(9) |
| Ag7-S5 | 2.466(4) | Ag7-S2 | 2.485(3) |
| Ag7-S3 | 2.528(3) | Ag7-Ag8 | 2.9957(13) |
| Ag8-S5 | 2.493(4) | Ag8-S1 | 2.509(3) |
| Ag8-S4 | 2.522(3) | S1-C11 | 1.764(11) |
| S2-C21 | 1.783(11) | S3-C31 | 1.769(13) |

FIG. 15

| | | | |
|---|---|---|---|
| S3-Ag3#4 | 2.642(3) | S4-C41B | 1.73(2) |
| S4-C41A | 1.83(3) | S4-Ag3#1 | 2.599(3) |
| S5-C51 | 1.695(16) | C11-C16B | 1.33(3) |
| C11-C16A | 1.35(3) | C11-C12B | 1.41(4) |
| C11-C12A | 1.42(3) | C12A-C13A | 1.43(4) |
| C13A-C14 | 1.55(4) | C15A-C14 | 1.35(3) |
| C15A-C16A | 1.39(4) | C17A-O11A | 1.14(4) |
| C17A-O12A | 1.48(5) | C17A-C14 | 1.55(2) |
| C14-C15B | 1.24(3) | C14-C13B | 1.45(4) |
| C14-C17B | 1.55(2) | C12B-C13B | 1.43(5) |
| C15B-C16B | 1.44(4) | C17B-O11B | 1.16(4) |
| C17B-O12B | 1.41(5) | C21-C26A | 1.30(3) |
| C21-C26B | 1.30(3) | C21-C22A | 1.41(4) |
| C21-C22B | 1.50(3) | C24-C25B | 1.20(3) |
| C24-C25A | 1.28(3) | C24-C23A | 1.43(4) |
| C24-C27B | 1.47(2) | C24-C27A | 1.47(2) |
| C24-C23B | 1.59(4) | C22A-C23A | 1.43(5) |
| C25A-C26A | 1.41(4) | C27A-O22A | 1.21(6) |
| C27A-O21A | 1.49(7) | C22B-C23B | 1.37(4) |
| C25B-C26B | 1.44(4) | C27B-O22B | 1.27(4) |
| C27B-O21B | 1.41(4) | C31-C36A | 1.35(3) |
| C31-C32B | 1.37(4) | C31-C32A | 1.42(3) |
| C31-C36B | 1.58(3) | C32A-C33A | 1.34(4) |
| C33A-C34A | 1.26(6) | C34A-C35A | 1.43(6) |
| C34A-C37A | 1.55(7) | C35A-C36A | 1.39(4) |
| O31A-C37A | 1.29(4) | O32A-C37A | 1.49(5) |
| C32B-C33B | 1.47(5) | C33B-C34B | 1.50(4) |
| C34B-C35B | 1.52(4) | C34B-C37B | 1.53(6) |
| C35B-C36B | 1.37(4) | C37B-O31B | 1.27(4) |

FIG. 15 cont.

| | | | |
|---|---|---|---|
| C37B-O32B | 1.28(4) | C41A-C42A | 1.34(4) |
| C41A-C46A | 1.39(4) | C42A-C43A | 1.42(4) |
| C43A-C44A | 1.39(5) | C44A-C45A | 1.37(5) |
| C44A-C47A | 1.53(3) | C45A-C46A | 1.39(4) |
| C47A-O41A | 1.21(4) | C47A-O42A | 1.24(4) |
| C41B-C46B | 1.34(4) | C41B-C42B | 1.41(4) |
| C42B-C43B | 1.42(4) | C43B-C44B | 1.41(4) |
| C44B-C45B | 1.30(4) | C44B-C47B | 1.53(3) |
| C45B-C46B | 1.43(4) | C47B-O41B | 1.22(3) |
| C47B-O42B | 1.22(3) | C51-C56B | 1.43(4) |
| C51-C52A | 1.43(4) | C51-C52B | 1.46(4) |
| C51-C56A | 1.47(3) | C54-C53A | 1.41(5) |
| C54-C53B | 1.44(5) | C54-C55A | 1.48(4) |
| C54-C55B | 1.49(5) | C54-C57 | 1.52(3) |
| C52A-C53A | 1.48(6) | C55A-C56A | 1.41(5) |
| O51A-C57 | 1.27(4) | O52A-C57 | 1.33(4) |
| C52B-C53B | 1.47(5) | C55B-C56B | 1.48(5) |
| O51B-C57 | 1.35(4) | O52B-C57 | 1.34(4) |

Symmetry transformations used to generate equivalent atoms:
1   -x+y, y+1, -z
2   x+1, y, -z
3   x-y+2, -y+1, z
4   -x+1, y+2, z

FIG. 15 cont.

Table 7 – Bond Angles (°) for $Ag_{44}$

| | | | |
|---|---|---|---|
| Ag2#4-Ag1-Ag6 | 113.71(3) | Ag2#4-Ag1-Ag1#4 | 60.40(2) |
| Ag6-Ag1-Ag1#4 | 165.72(2) | Ag2#4-Ag1-Ag1#3 | 108.27(2) |
| Ag6-Ag1-Ag1#3 | 114.09(3) | Ag1#4-Ag1-Ag1#3 | 60.0 |
| Ag2#4-Ag1-Ag5#4 | 61.24(2) | Ag6-Ag1-Ag5#4 | 130.34(3) |
| Ag1#4-Ag1-Ag5#4 | 60.22(3) | Ag1#3-Ag1-Ag5#4 | 113.79(2) |
| Ag2#4-Ag1-Ag5 | 166.22(3) | Ag6-Ag1-Ag5 | 68.97(2) |
| Ag1#4-Ag1-Ag5 | 113.52(2) | Ag1#3-Ag1-Ag5 | 59.92(3) |
| Ag5#4-Ag1-Ag5 | 128.36(3) | Ag2#4-Ag1-Ag2 | 107.83(3) |
| Ag6-Ag1-Ag2 | 60.32(2) | Ag1#4-Ag1-Ag2 | 107.75(2) |
| Ag1#3-Ag1-Ag2 | 59.74(2) | Ag5#4-Ag1-Ag2 | 166.21(3) |
| Ag5-Ag1-Ag2 | 60.90(2) | Ag2#4-Ag1-Ag2#1 | 59.956(15) |
| Ag6-Ag1-Ag2#1 | 59.94(2) | Ag1#4-Ag1-Ag2#1 | 108.067(18) |
| Ag1#3-Ag1-Ag2#1 | 107.669(18) | Ag5#4-Ag1-Ag2#1 | 115.44(3) |
| Ag5-Ag1-Ag2#1 | 114.72(3) | Ag2-Ag1-Ag2#1 | 59.740(15) |
| Ag2#4-Ag1-Ag3#4 | 60.66(2) | Ag6-Ag1-Ag3#4 | 67.39(2) |
| Ag1#4-Ag1-Ag3#4 | 115.02(3) | Ag1#3-Ag1-Ag3#4 | 166.296(19) |
| Ag5#4-Ag1-Ag3#4 | 69.34(2) | Ag5-Ag1-Ag3#4 | 129.69(3) |
| Ag2-Ag1-Ag3#4 | 113.97(3) | Ag2#1-Ag1-Ag3#4 | 60.50(2) |
| Ag2#4-Ag1-Ag4 | 114.74(2) | Ag6-Ag1-Ag4 | 129.91(3) |
| Ag1#4-Ag1-Ag4 | 60.509(13) | Ag1#3-Ag1-Ag4 | 60.508(13) |
| Ag5#4-Ag1-Ag4 | 67.26(2) | Ag5-Ag1-Ag4 | 67.154(19) |
| Ag2-Ag1-Ag4 | 114.15(2) | Ag2#1-Ag1-Ag4 | 166.10(3) |
| Ag3#4-Ag1-Ag4 | 130.03(3) | Ag1#3-Ag2-Ag6#2 | 114.97(3) |
| Ag1#3-Ag2-Ag2#1 | 108.246(18) | Ag6#2-Ag2-Ag2#1 | 112.89(3) |
| Ag1#3-Ag2-Ag2#2 | 60.551(17) | Ag6#2-Ag2-Ag2#2 | 60.24(3) |
| Ag2#1-Ag2-Ag2#2 | 107.61(2) | Ag1#3-Ag2-Ag1 | 59.87(3) |
| Ag6#2-Ag2-Ag1 | 165.50(3) | Ag2#1-Ag2-Ag1 | 60.335(17) |
| Ag2#2-Ag2-Ag1 | 108.120(18) | Ag1#3-Ag2-Ag6 | 113.49(3) |

FIG. 16

| | | | |
|---|---|---|---|
| Ag6#2-Ag2-Ag6 | 130.25(3) | Ag2#1-Ag2-Ag6 | 59.87(2) |
| Ag2#2-Ag2-Ag6 | 165.07(2) | Ag1-Ag2-Ag6 | 59.52(2) |
| Ag1#3-Ag2-Ag1#2 | 108.46(3) | Ag6#2-Ag2-Ag1#2 | 59.50(2) |
| Ag2#1-Ag2-Ag1#2 | 59.49(2) | Ag2#2-Ag2-Ag1#2 | 59.92(2) |
| Ag1-Ag2-Ag1#2 | 107.95(3) | Ag6-Ag2-Ag1#2 | 113.69(3) |
| Ag1#3-Ag2-Ag3 | 60.20(2) | Ag6#2-Ag2-Ag3 | 69.12(2) |
| Ag2#1-Ag2-Ag3 | 165.95(2) | Ag2#2-Ag2-Ag3 | 60.54(2) |
| Ag1-Ag2-Ag3 | 114.14(3) | Ag6-Ag2-Ag3 | 130.39(3) |
| Ag1#2-Ag2-Ag3 | 114.48(3) | Ag1#3-Ag2-Ag3#1 | 166.11(3) |
| Ag6#2-Ag2-Ag3#1 | 66.93(2) | Ag2#1-Ag2-Ag3#1 | 60.25(3) |
| Ag2#2-Ag2-Ag3#1 | 113.47(3) | Ag1-Ag2-Ag3#1 | 114.59(3) |
| Ag6-Ag2-Ag3#1 | 68.87(2) | Ag1#2-Ag2-Ag3#1 | 59.76(2) |
| Ag3-Ag2-Ag3#1 | 129.72(3) | Ag1#3-Ag2-Ag5 | 59.48(2) |
| Ag6#2-Ag2-Ag5 | 131.62(3) | Ag2#1-Ag2-Ag5 | 113.96(3) |
| Ag2#2-Ag2-Ag5 | 114.40(3) | Ag1-Ag2-Ag5 | 59.46(2) |
| Ag6-Ag2-Ag5 | 68.09(2) | Ag1#2-Ag2-Ag5 | 165.24(3) |
| Ag3-Ag2-Ag5 | 68.48(2) | Ag3#1-Ag2-Ag5 | 130.67(3) |
| S4#2-Ag3-S1 | 108.34(9) | S4#2-Ag3-S3#3 | 105.65(9) |
| S1-Ag3-S3#3 | 106.66(9) | S4#2-Ag3-Ag1#3 | 140.43(6) |
| S1-Ag3-Ag1#3 | 105.15(7) | S3#3-Ag3-Ag1#3 | 83.91(6) |
| S4#2-Ag3-Ag2 | 105.39(7) | S1-Ag3-Ag2 | 82.06(6) |
| S3#3-Ag3-Ag2 | 142.90(6) | Ag1#3-Ag3-Ag2 | 59.14(2) |
| S4#2-Ag3-Ag2#2 | 80.87(6) | S1-Ag3-Ag2#2 | 141.10(6) |
| S3#3-Ag3-Ag2#2 | 106.80(7) | Ag1#3-Ag3-Ag2#2 | 59.75(2) |
| Ag2-Ag3-Ag2#2 | 59.21(2) | S4#2-Ag3-Ag6#3 | 100.19(7) |
| S1-Ag3-Ag6#3 | 148.40(7) | S3#3-Ag3-Ag6#3 | 51.10(6) |
| Ag1#3-Ag3-Ag6#3 | 55.84(2) | Ag2-Ag3-Ag6#3 | 103.49(2) |
| Ag2#2-Ag3-Ag6#3 | 55.95(2) | S4#2-Ag3-Ag5 | 149.85(7) |
| S1-Ag3-Ag5 | 50.27(6) | S3#3-Ag3-Ag5 | 101.54(6) |
| Ag1#3-Ag3-Ag5 | 54.96(2) | Ag2-Ag3-Ag5 | 55.93(2) |

FIG. 16 cont.

| | | | |
|---|---|---|---|
| Ag2#2-Ag3-Ag5 | 103.57(2) | Ag6#3-Ag3-Ag5 | 106.96(2) |
| S4#2-Ag3-Ag6#2 | 50.45(6) | S1-Ag3-Ag6#2 | 100.93(6) |
| S3#3-Ag3-Ag6#2 | 148.71(7) | Ag1#3-Ag3-Ag6#2 | 103.03(2) |
| Ag2-Ag3-Ag6#2 | 55.00(2) | Ag2#2-Ag3-Ag6#2 | 55.15(2) |
| Ag6#3-Ag3-Ag6#2 | 107.70(2) | Ag5-Ag3-Ag6#2 | 107.40(2) |
| S2#4-Ag4-S2#3 | 105.83(7) | S2#4-Ag4-S2 | 105.82(7) |
| S2#3-Ag4-S2 | 105.82(7) | S2#4-Ag4-Ag1 | 107.53(6) |
| S2#3-Ag4-Ag1 | 141.53(6) | S2-Ag4-Ag1 | 82.91(6) |
| S2#4-Ag4-Ag1#4 | 82.91(6) | S2#3-Ag4-Ag1#4 | 107.53(6) |
| S2-Ag4-Ag1#4 | 141.53(6) | Ag1-Ag4-Ag1#4 | 58.99(3) |
| S2#4-Ag4-Ag1#3 | 141.53(6) | S2#3-Ag4-Ag1#3 | 82.91(6) |
| S2-Ag4-Ag1#3 | 107.54(6) | Ag1-Ag4-Ag1#3 | 58.99(3) |
| Ag1#4-Ag4-Ag1#3 | 58.99(3) | S2#4-Ag4-Ag5#4 | 51.86(6) |
| S2#3-Ag4-Ag5#4 | 150.42(6) | S2-Ag4-Ag5#4 | 99.73(6) |
| Ag1-Ag4-Ag5#4 | 55.73(2) | Ag1#4-Ag4-Ag5#4 | 55.91(2) |
| Ag1#3-Ag4-Ag5#4 | 103.51(3) | S2#4-Ag4-Ag5#3 | 99.73(6) |
| S2#3-Ag4-Ag5#3 | 51.86(6) | S2-Ag4-Ag5#3 | 150.42(6) |
| Ag1-Ag4-Ag5#3 | 103.51(3) | Ag1#4-Ag4-Ag5#3 | 55.73(2) |
| Ag1#3-Ag4-Ag5#3 | 55.91(2) | Ag5#4-Ag4-Ag5#3 | 107.75(2) |
| S2#4-Ag4-Ag5 | 150.42(6) | S2#3-Ag4-Ag5 | 99.74(6) |
| S2-Ag4-Ag5 | 51.86(6) | Ag1-Ag4-Ag5 | 55.91(2) |
| Ag1#4-Ag4-Ag5 | 103.50(3) | Ag1#3-Ag4-Ag5 | 55.73(2) |
| Ag5#4-Ag4-Ag5 | 107.75(2) | Ag5#3-Ag4-Ag5 | 107.75(2) |
| S1-Ag5-S2 | 130.24(8) | S1-Ag5-Ag1#3 | 108.49(6) |
| S2-Ag5-Ag1#3 | 110.74(6) | S1-Ag5-Ag1 | 142.52(7) |
| S2-Ag5-Ag1 | 84.77(6) | Ag1#3-Ag5-Ag1 | 59.87(3) |
| S1-Ag5-Ag2 | 83.46(6) | S2-Ag5-Ag2 | 143.69(6) |
| Ag1#3-Ag5-Ag2 | 59.30(2) | Ag1-Ag5-Ag2 | 59.64(2) |
| S1-Ag5-Ag8 | 51.67(6) | S2-Ag5-Ag8 | 104.10(6) |
| Ag1#3-Ag5-Ag8 | 143.46(3) | Ag1-Ag5-Ag8 | 114.35(3) |

FIG. 16 cont.

| | | | |
|---|---|---|---|
| Ag2-Ag5-Ag8 | 86.04(3) | S1-Ag5-Ag7 | 104.62(6) |
| S2-Ag5-Ag7 | 50.74(6) | Ag1#3-Ag5-Ag7 | 145.15(3) |
| Ag1-Ag5-Ag7 | 87.07(3) | Ag2-Ag5-Ag7 | 115.22(3) |
| Ag8-Ag5-Ag7 | 57.64(3) | S1-Ag5-Ag4 | 150.57(7) |
| S2-Ag5-Ag4 | 53.79(6) | Ag1#3-Ag5-Ag4 | 57.01(2) |
| Ag1-Ag5-Ag4 | 56.94(2) | Ag2-Ag5-Ag4 | 105.14(3) |
| Ag8-Ag5-Ag4 | 154.63(3) | Ag7-Ag5-Ag4 | 97.09(3) |
| S1-Ag5-Ag6 | 99.73(7) | S2-Ag5-Ag6 | 99.70(6) |
| Ag1#3-Ag5-Ag6 | 103.42(2) | Ag1-Ag5-Ag6 | 55.32(2) |
| Ag2-Ag5-Ag6 | 55.49(2) | Ag8-Ag5-Ag6 | 59.07(2) |
| Ag7-Ag5-Ag6 | 59.82(2) | Ag4-Ag5-Ag6 | 108.37(3) |
| S1-Ag5-Ag3 | 52.87(6) | S2-Ag5-Ag3 | 151.83(7) |
| Ag1#3-Ag5-Ag3 | 55.70(2) | Ag1-Ag5-Ag3 | 104.09(2) |
| Ag2-Ag5-Ag3 | 55.60(2) | Ag8-Ag5-Ag3 | 96.54(3) |
| Ag7-Ag5-Ag3 | 154.12(3) | Ag4-Ag5-Ag3 | 108.61(2) |
| Ag6-Ag5-Ag3 | 107.35(3) | S3-Ag6-S4 | 129.28(9) |
| S3-Ag6-Ag1 | 86.54(6) | S4-Ag6-Ag1 | 141.92(7) |
| S3-Ag6-Ag2#1 | 111.14(6) | S4-Ag6-Ag2#1 | 107.78(6) |
| Ag1-Ag6-Ag2#1 | 60.56(2) | S3-Ag6-Ag2 | 146.08(7) |
| S4-Ag6-Ag2 | 82.35(6) | Ag1-Ag6-Ag2 | 60.16(2) |
| Ag2#1-Ag6-Ag2 | 59.89(2) | S3-Ag6-Ag8 | 103.36(6) |
| S4-Ag6-Ag8 | 51.89(6) | Ag1-Ag6-Ag8 | 114.62(3) |
| Ag2#1-Ag6-Ag8 | 144.40(3) | Ag2-Ag6-Ag8 | 86.50(3) |
| S3-Ag6-Ag3#4 | 54.28(6) | S4-Ag6-Ag3#4 | 151.00(7) |
| Ag1-Ag6-Ag3#4 | 56.76(2) | Ag2#1-Ag6-Ag3#4 | 57.12(2) |
| Ag2-Ag6-Ag3#4 | 105.48(3) | Ag8-Ag6-Ag3#4 | 153.98(3) |
| S3-Ag6-Ag7 | 51.48(6) | S4-Ag6-Ag7 | 105.12(6) |
| Ag1-Ag6-Ag7 | 86.69(3) | Ag2#1-Ag6-Ag7 | 145.36(3) |
| Ag2-Ag6-Ag7 | 115.19(3) | Ag8-Ag6-Ag7 | 57.28(3) |
| Ag3#4-Ag6-Ag7 | 96.76(3) | S3-Ag6-Ag5 | 100.82(6) |

FIG. 16 cont.

| | | | |
|---|---|---|---|
| S4-Ag6-Ag5 | 99.32(7) | Ag1-Ag6-Ag5 | 55.71(2) |
| Ag2#1-Ag6-Ag5 | 104.80(2) | Ag2-Ag6-Ag5 | 56.42(2) |
| Ag8-Ag6-Ag5 | 58.95(2) | Ag3#4-Ag6-Ag5 | 108.30(3) |
| Ag7-Ag6-Ag5 | 58.86(2) | S3-Ag6-Ag3#1 | 150.03(7) |
| S4-Ag6-Ag3#1 | 51.95(6) | Ag1-Ag6-Ag3#1 | 104.92(2) |
| Ag2#1-Ag6-Ag3#1 | 55.88(2) | Ag2-Ag6-Ag3#1 | 55.98(2) |
| Ag8-Ag6-Ag3#1 | 96.89(3) | Ag3#4-Ag6-Ag3#1 | 108.98(2) |
| Ag7-Ag6-Ag3#1 | 154.12(3) | Ag5-Ag6-Ag3#1 | 108.54(3) |
| S5-Ag7-S2 | 137.17(11) | S5-Ag7-S3 | 112.68(11) |
| S2-Ag7-S3 | 109.85(9) | S5-Ag7-Ag8 | 53.24(9) |
| S2-Ag7-Ag8 | 109.36(8) | S3-Ag7-Ag8 | 106.55(7) |
| S5-Ag7-Ag5 | 110.92(10) | S2-Ag7-Ag5 | 53.17(7) |
| S3-Ag7-Ag5 | 103.05(6) | Ag8-Ag7-Ag5 | 60.91(3) |
| S5-Ag7-Ag6 | 99.33(9) | S2-Ag7-Ag6 | 102.88(6) |
| S3-Ag7-Ag6 | 51.64(7) | Ag8-Ag7-Ag6 | 60.63(3) |
| Ag5-Ag7-Ag6 | 61.32(2) | S5-Ag8-S1 | 136.29(11) |
| S5-Ag8-S4 | 116.83(11) | S1-Ag8-S4 | 106.65(9) |
| S5-Ag8-Ag7 | 52.43(9) | S1-Ag8-Ag7 | 109.03(8) |
| S4-Ag8-Ag7 | 110.22(7) | S5-Ag8-Ag5 | 110.67(9) |
| S1-Ag8-Ag5 | 52.67(7) | S4-Ag8-Ag5 | 102.35(6) |
| Ag7-Ag8-Ag5 | 61.45(3) | S5-Ag8-Ag6 | 99.88(9) |
| S1-Ag8-Ag6 | 102.92(6) | S4-Ag8-Ag6 | 52.58(7) |
| Ag7-Ag8-Ag6 | 62.09(3) | Ag5-Ag8-Ag6 | 61.97(2) |
| C11-S1-Ag8 | 112.0(4) | C11-S1-Ag5 | 110.4(5) |
| Ag8-S1-Ag5 | 75.66(8) | C11-S1-Ag3 | 113.3(4) |
| Ag8-S1-Ag3 | 132.85(10) | Ag5-S1-Ag3 | 76.85(7) |
| C21-S2-Ag7 | 108.8(4) | C21-S2-Ag5 | 108.5(5) |
| Ag7-S2-Ag5 | 76.09(8) | C21-S2-Ag4 | 115.1(4) |
| Ag7-S2-Ag4 | 132.77(10) | Ag5-S2-Ag4 | 74.35(7) |
| C31-S3-Ag7 | 107.8(4) | C31-S3-Ag6 | 100.4(5) |

FIG. 16 cont.

| | | | |
|---|---|---|---|
| Ag7-S3-Ag6 | 76.88(8) | C31-S3-Ag3#4 | 116.3(4) |
| Ag7-S3-Ag3#4 | 130.62(10) | Ag6-S3-Ag3#4 | 74.61(7) |
| C41B-S4-C41A | 14.2(11) | C41B-S4-Ag8 | 110.2(8) |
| C41A-S4-Ag8 | 111.6(8) | C41B-S4-Ag6 | 121.9(9) |
| C41A-S4-Ag6 | 108.1(9) | Ag8-S4-Ag6 | 75.53(8) |
| C41B-S4-Ag3#1 | 114.4(8) | C41A-S4-Ag3#1 | 110.5(8) |
| Ag8-S4-Ag3#1 | 135.23(10) | Ag6-S4-Ag3#1 | 77.59(7) |
| C51-S5-Ag7 | 111.9(5) | C51-S5-Ag8 | 104.9(6) |
| Ag7-S5-Ag8 | 74.33(9) | C16B-C11-C16A | 85.7(19) |
| C16B-C11-C12B | 116.(2) | C16A-C11-C12B | 51.3(18) |
| C16B-C11-C12A | 59.0(16) | C16A-C11-C12A | 122.3(19) |
| C12B-C11-C12A | 103.(2) | C16B-C11-S1 | 122.9(14) |
| C16A-C11-S1 | 118.0(15) | C12B-C11-S1 | 118.7(17) |
| C12A-C11-S1 | 119.5(14) | C11-C12A-C13A | 120.(3) |
| C12A-C13A-C14 | 114.(3) | C14-C15A-C16A | 120.(3) |
| C11-C16A-C15A | 122.(3) | O11A-C17A-O12A | 130.(3) |
| O11A-C17A-C14 | 129.(4) | O12A-C17A-C14 | 97.(2) |
| C15B-C14-C15A | 91.(2) | C15B-C14-C13B | 123.(2) |
| C15A-C14-C13B | 51.2(19) | C15B-C14-C13A | 59.5(19) |
| C15A-C14-C13A | 122.(2) | C13B-C14-C13A | 101.(2) |
| C15B-C14-C17A | 119.(2) | C15A-C14-C17A | 133.(2) |
| C13B-C14-C17A | 118.(2) | C13A-C14-C17A | 105.(2) |
| C15B-C14-C17B | 115.(2) | C15A-C14-C17B | 112.(2) |
| C13B-C14-C17B | 118.(2) | C13A-C14-C17B | 126.(2) |
| C17A-C14-C17B | 24.5(17) | C11-C12B-C13B | 121.(3) |
| C12B-C13B-C14 | 115.(3) | C14-C15B-C16B | 120.(3) |
| C11-C16B-C15B | 122.(2) | O11B-C17B-O12B | 119.(3) |
| O11B-C17B-C14 | 120.(3) | O12B-C17B-C14 | 107.(3) |
| C26A-C21-C26B | 86.(2) | C26A-C21-C22A | 119.(2) |
| C26B-C21-C22A | 56.9(19) | C26A-C21-C22B | 59.6(18) |

FIG. 16 cont.

| | | | |
|---|---|---|---|
| C26B-C21-C22B | 119.3(19) | C22A-C21-C22B | 96.(2) |
| C26A-C21-S2 | 123.4(16) | C26B-C21-S2 | 122.1(16) |
| C22A-C21-S2 | 117.2(18) | C22B-C21-S2 | 118.7(14) |
| C25B-C24-C25A | 87.(2) | C25B-C24-C23A | 59.(2) |
| C25A-C24-C23A | 121.(2) | C25B-C24-C27B | 128.(3) |
| C25A-C24-C27B | 124.(2) | C23A-C24-C27B | 115.(2) |
| C25B-C24-C27A | 105.(3) | C25A-C24-C27A | 121.(3) |
| C23A-C24-C27A | 115.(4) | C27B-C24-C27A | 25.(3) |
| C25B-C24-C23B | 122.(2) | C25A-C24-C23B | 57.6(18) |
| C23A-C24-C23B | 99.(2) | C27B-C24-C23B | 110.(2) |
| C27A-C24-C23B | 132.(3) | C21-C22A-C23A | 121.(3) |
| C24-C23A-C22A | 115.(3) | C24-C25A-C26A | 124.(3) |
| C21-C26A-C25A | 120.(3) | O22A-C27A-C24 | 114.(5) |
| O22A-C27A-O21A | 109.(4) | C24-C27A-O21A | 107.(4) |
| C23B-C22B-C21 | 122.(3) | C22B-C23B-C24 | 112.(3) |
| C24-C25B-C26B | 124.(3) | C21-C26B-C25B | 120.(3) |
| O22B-C27B-O21B | 124.(2) | O22B-C27B-C24 | 125.(3) |
| O21B-C27B-C24 | 110.(2) | C36A-C31-C32B | 115.(2) |
| C36A-C31-C32A | 117.(2) | C32B-C31-C32A | 27.5(10) |
| C36A-C31-C36B | 23.6(14) | C32B-C31-C36B | 124.(2) |
| C32A-C31-C36B | 113.5(17) | C36A-C31-S3 | 122.3(16) |
| C32B-C31-S3 | 117.2(18) | C32A-C31-S3 | 120.3(14) |
| C36B-C31-S3 | 118.8(14) | C33A-C32A-C31 | 121.(3) |
| C34A-C33A-C32A | 121.(4) | C33A-C34A-C35A | 122.(6) |
| C33A-C34A-C37A | 128.(5) | C35A-C34A-C37A | 110.(4) |
| C36A-C35A-C34A | 117.(4) | C31-C36A-C35A | 121.(3) |
| O31A-C37A-O32A | 118.(3) | O31A-C37A-C34A | 109.(4) |
| O32A-C37A-C34A | 128.(4) | C31-C32B-C33B | 118.(3) |
| C32B-C33B-C34B | 117.(3) | C33B-C34B-C35B | 125.(4) |
| C33B-C34B-C37B | 112.(3) | C35B-C34B-C37B | 123.(3) |

FIG. 16 cont.

| | | | |
|---|---|---|---|
| C36B-C35B-C34B | 114.(3) | C35B-C36B-C31 | 121.(3) |
| O31B-C37B-O32B | 124.(4) | O31B-C37B-C34B | 115.(3) |
| O32B-C37B-C34B | 108.(3) | C42A-C41A-C46A | 117.(3) |
| C42A-C41A-S4 | 121.(2) | C46A-C41A-S4 | 121.(2) |
| C41A-C42A-C43A | 123.(3) | C44A-C43A-C42A | 121.(3) |
| C45A-C44A-C43A | 113.(4) | C45A-C44A-C47A | 127.(4) |
| C43A-C44A-C47A | 116.(4) | C44A-C45A-C46A | 125.(3) |
| C45A-C46A-C41A | 119.(3) | O41A-C47A-O42A | 129.(4) |
| O41A-C47A-C44A | 116.(4) | O42A-C47A-C44A | 111.(4) |
| C46B-C41B-C42B | 119.(2) | C46B-C41B-S4 | 123.(2) |
| C42B-C41B-S4 | 117.7(19) | C41B-C42B-C43B | 119.(3) |
| C44B-C43B-C42B | 118.(3) | C45B-C44B-C43B | 121.(2) |
| C45B-C44B-C47B | 120.(2) | C43B-C44B-C47B | 115.(2) |
| C44B-C45B-C46B | 119.(3) | C41B-C46B-C45B | 122.(3) |
| O41B-C47B-O42B | 121.(3) | O41B-C47B-C44B | 120.(3) |
| O42B-C47B-C44B | 117.(3) | C56B-C51-C52A | 60.(2) |
| C56B-C51-C52B | 122.(3) | C52A-C51-C52B | 88.(2) |
| C56B-C51-C56A | 94.(2) | C52A-C51-C56A | 121.(2) |
| C52B-C51-C56A | 59.(2) | C56B-C51-S5 | 117.(2) |
| C52A-C51-S5 | 122.(2) | C52B-C51-S5 | 121.(2) |
| C56A-C51-S5 | 117.1(17) | C53A-C54-C53B | 88.(3) |
| C53A-C54-C55A | 124.(3) | C53B-C54-C55A | 63.(2) |
| C53A-C54-C55B | 63.(2) | C53B-C54-C55B | 127.(3) |
| C55A-C54-C55B | 96.(3) | C53A-C54-C57 | 115.(3) |
| C53B-C54-C57 | 119.(3) | C55A-C54-C57 | 121.(2) |
| C55B-C54-C57 | 114.(3) | C51-C52A-C53A | 123.(3) |
| C54-C53A-C52A | 114.(4) | C56A-C55A-C54 | 120.(3) |
| C55A-C56A-C51 | 118.(3) | C51-C52B-C53B | 121.(4) |
| C54-C53B-C52B | 115.(4) | C56B-C55B-C54 | 113.(3) |

FIG. 16 cont.

| | | | |
|---|---|---|---|
| C54-C53B-C52B | 115.(4) | C56B-C55B-C54 | 113.(3) |
| C51-C56B-C55B | 122.(3) | O51A-C57-O52A | 122.(3) |
| O51A-C57-O52B | 66.(3) | O52A-C57-O52B | 110.(3) |
| O51A-C57-O51B | 81.(3) | O52A-C57-O51B | 59.(2) |
| O52B-C57-O51B | 132.(3) | O51A-C57-C54 | 115.(3) |
| O52A-C57-C54 | 116.(3) | O52B-C57-C54 | 117.(3) |
| O51B-C57-C54 | 109.(3) | | |

Symmetry transformations used to generate equivalent atoms:
1  -x+y, y+1, -z
2  x+1, y, -z
3  x-y+2, -y+1, z
4  -x+1, y+2, z

FIG. 16 cont.

Table 8 – Anisotropic Atomic Displacement Parameters (Å$^2$) for Ag$_{44}$

| | U$_{11}$ | U$_{22}$ | U$_{33}$ | U$_{23}$ | U$_{13}$ | U$_{12}$ |
|---|---|---|---|---|---|---|
| Ag1 | 0.0268(3) | 0.0270(3) | 0.0225(3) | -0.0006(2) | -0.0004(2) | 0.0143(3) |
| Ag2 | 0.0269(3) | 0.0275(3) | 0.0232(3) | -0.0008(2) | 0.0002(2) | 0.0137(3) |
| Ag3 | 0.0335(3) | 0.0257(3) | 0.0342(4) | -0.0039(2) | -0.0022(3) | 0.0104(3) |
| Ag4 | 0.0393(4) | 0.0393(4) | 0.0200(5) | 0 | 0 | 0.01967(19) |
| Ag5 | 0.0376(4) | 0.0485(4) | 0.0344(4) | -0.0148(3) | -0.0115(3) | 0.0227(3) |
| Ag6 | 0.0327(4) | 0.0526(4) | 0.0386(4) | -0.0090(3) | -0.0069(3) | 0.0258(3) |
| Ag7 | 0.0624(5) | 0.0751(6) | 0.0437(5) | -0.0151(4) | -0.0158(4) | 0.0449(5) |
| Ag8 | 0.0433(4) | 0.0702(6) | 0.0560(5) | -0.0213(4) | -0.0129(4) | 0.0286(4) |
| S1 | 0.0526(15) | 0.0528(15) | 0.0474(15) | -0.0195(12) | -0.0196(12) | 0.0283(13) |
| S2 | 0.0479(14) | 0.0667(17) | 0.0328(13) | -0.0159(12) | -0.0116(11) | 0.0297(13) |
| S3 | 0.0427(14) | 0.0594(16) | 0.0528(16) | -0.0125(12) | -0.0121(11) | 0.0322(13) |
| S4 | 0.0385(13) | 0.0700(18) | 0.0412(14) | -0.0055(12) | -0.0046(11) | 0.0306(13) |
| S5 | 0.0603(19) | 0.104(3) | 0.079(2) | -0.025(2) | -0.0291(17) | 0.047(2) |
| C11 | 0.067(8) | 0.064(8) | 0.053(7) | -0.020(6) | -0.023(6) | 0.040(7) |
| C14 | 0.120(13) | 0.105(12) | 0.082(10) | -0.055(9) | -0.047(10) | 0.075(11) |
| C21 | 0.057(7) | 0.084(9) | 0.047(7) | -0.024(6) | -0.013(5) | 0.038(7) |
| C24 | 0.101(12) | 0.118(14) | 0.055(9) | -0.042(9) | -0.014(8) | 0.044(11) |
| C31 | 0.076(9) | 0.095(10) | 0.064(8) | -0.027(7) | -0.021(7) | 0.060(8) |
| C51 | 0.065(9) | 0.093(11) | 0.108(12) | -0.016(9) | -0.014(8) | 0.046(9) |
| C54 | 0.142(18) | 0.133(17) | 0.110(15) | -0.059(13) | -0.066(14) | 0.072(15) |

FIG. 17

ULTRASTABLE SILVER NANOPARTICLES

RELATED APPLICATIONS

The present application is a national stage application filed under 35 U.S.C. §371 of international application PCT/US2014/027707, filed under the authority of the Patent Cooperation treaty on Mar. 14, 2014, published; which claims priority to U.S. Provisional Application Ser. No. 61/789,443, filed under 35 U.S.C. §111(b) on Mar. 15, 2013, and U.S. Provisional Application Ser. No. 61/867,912, filed under 35 U.S.C. §111(b) on Aug. 20, 2013, the disclosures of which are incorporated herein by reference in their entirety.

STATEMENT REGARDING FEDERALLY SPONSORED RESEARCH

This invention was made with government support under Grant Number 0955148 awarded by the National Science Foundation. The government has certain rights in this invention.

BACKGROUND OF THE INVENTION

Noble-metal nanoparticles have had a substantial impact across a diverse range of fields, including catalysis, sensing, photochemistry, optoelectronics, energy conversion, and medicine. Gold nanoparticles have long been favored over silver nanoparticles in part because of their stability. However, silver nanoparticles have potentially more applications than gold nanoparticles due to their superior optical properties, bioactivity, diversity of chemical and photochemical properties, and lower cost.

The development of silver nanoparticles has been hindered by the instability of silver nanoparticles. The ease of oxidation has limited the development of these materials. A further difficulty with silver nanoparticle development has been size distribution. Single-sized products have generally only been isolated by attrition, wherein the less stable sizes are either destroyed or converted into the most stable size. For these reasons, despite the possible applications, chemically inert and long-term stable silver nanomaterials remain unrealized.

SUMMARY OF THE INVENTION

Provided herein is a compound comprising the formula $M_4Ag_{44}(SR)_{30}$, or the formula $M_4Ag_{44}(SeR)_{30}$, wherein M is a metal selected from the group consisting of Cs, Na, K, Li, Fr, and Rb; SR is a mercaptophenyl ligand; and SeR is a benzeneselenol ligand; and salts, isomers, stereoisomers, entantiomers, racemates, solvates, hydrates, polymorphs, and prodrugs thereof. In certain embodiments, the mercaptophenyl ligand is selected from the group consisting of p-mercaptobenzoic acid (p-MBA), p-mercaptophenyl alcohol, and 4-mercaptophenol. In certain embodiments, the mercaptophenyl ligand comprises p-mercaptobenzoic acid.

In certain embodiments, the compound further comprises coordinating molecules selected from the group consisting of: deprotonated methanol ions, deprotonated ethanol ions, hydroxide ions, citrate, acetate, DMSO, DMF, pyridine, ammonia, acetone, acetonitrile, ethers, phosphines, and combinations thereof. In certain embodiments, the compound has a core comprising coordination sites, and the coordinating molecules stabilize the compound by binding to the coordination sites. In certain embodiments, one or more of the coordinating molecules is displaced by one or more of a pharmaceutical agent, a fluorophore, or a carbohydrate, covalently bonded through a sulfur or selenium linkage at a coordination site.

In certain embodiments, the compound comprises a $Ag_{32}$ core and a protecting layer of $Ag_2S_5$ capping structures. In certain embodiments, the compound comprises a $Ag_{32}$ core and a protecting layer of $Ag_2Se_5$ capping structures.

Further provided herein is a silver cluster molecule comprising a 32-silver-atom dodecahedral core consisting of a 12-silver-atom icosahedron encapsulated by a 20-silver-atom dodecahedron; and 30 coordinating ligands. In certain embodiments, the coordinating ligands comprise p-MBA. In certain embodiments, the dodecahedral core comprises icosahedral symmetry.

In certain embodiments, the silver cluster molecule further comprises a protecting layer of $Ag_2S_5$ capping mounts, wherein four sulfur atoms connect the mounts to the core. In certain embodiments, the silver atoms in the icosahedral core do not contact the coordinating ligands. In certain embodiments, 24 of the coordinating ligands comprise atoms defining a rhombicuboctahedron capped with six $Ag_2S$ units.

Further provided herein is a method of making silver nanoparticles, the method comprising the steps of: preparing a Ag(I)—SR or Ag(I)—SeR precursor compound, reducing the Ag(I)—SR or Ag(I)—SeR precursor compound to grow silver nanoparticles, and removing by-products to isolate the silver nanoparticles, wherein SR is a mercaptophenyl ligand. In certain embodiments, the mercaptophenyl ligand comprises p-mercaptobenzoic acid. In certain embodiments, preparing the Ag(I)—SR or Ag(I)—SeR precursor compound comprises adding a solvent to a mixture of silver nitrate and a mercaptophenyl ligand, and a base to solubilize the precursor. In certain embodiments, the solvent is selected from the group consisting of: water, ethanol, methanol, DMF, DMSO, pyridine, acetone, acetonitrile, ethers, phosphines, and mixtures thereof. In certain embodiments, the base is selected from the group consisting of: CsOH, LiOH, NaOH, KOH, $NH_4OH$, $CsCH_3CO_2$, $CsCO_3$, $LiCH_3CO_2$, $Li_2CO_3$, $NaCH_3CO_2$, $Na_2CO_3$, $KCH_3CO_2$, $K_2CO_3$, $NH_4CH_3CO_2$, and combinations thereof. In certain embodiments, the method further comprises adjusting the pH to about 9 to solubilize the Ag(I)—SR or Ag(I)—SeR precursor. In certain embodiments, the method further comprises adjusting the pH to about 12 to stabilize the silver nanoparticles. In certain embodiments, the reducing comprises adding a reducing agent to the Ag(I)—SR precursor compound, wherein the reducing agent is selected from the group consisting of: $NaBH_4$, $LiBH_4$, $KBH_4$, $Al(BH_4)_3$, and combinations thereof.

In certain embodiments, the by-products are removed by precipitating the silver nanoparticles, and collecting the precipitated silver nanoparticles. In particular embodiments, the nanoparticles are precipitated by the addition of a non-solvent selected from the group consisting of: methanol, DMF, toluene, and combinations thereof. In particular embodiments, the nanoparticles are precipitated by cooling.

In certain embodiments, the method further comprises a coordinating molecule exchange step.

Further provided are the silver nanoparticles made from the method of making silver nanoparticles described herein. Also provided is a cosmetic product comprising a compound described herein.

BRIEF DESCRIPTION OF THE DRAWINGS

The patent or application file contains one or more drawings executed in color and/or one or more photographs.

Copies of this patent or patent application publication with color drawing(s) and/or photograph(s) will be provided by the U.S. Patent and Trademark Office upon request and payment of the necessary fees.

FIG. 1A is a complete cluster structure showing a silver core and p-MBA ligands. FIG. 1B is a space-filling view down a three-fold axis. Note face-to-face and edge-to-edge π stacking in the groupings of two and three ligands, resulting in considerable void space. FIG. 1C shows the $Ag_{32}$ excavated-dodecahedral core consists of an inner 12-atom (hollow) icosahedron (red) whose atoms do not contact sulfur, encapsulated by a 20-atom dodecahedron (green). FIG. 1D shows the complete $Ag_{32}$ excavated-dodecahedral core. The eight atoms of the dodecahedron that are colored light green define a cube, with pairs of dark-green Ag atoms located above the faces. FIG. 1E shows sulfur atoms (yellow) are arranged in a slightly distorted rhombicuboctahedron with S atoms in the triangular faces coordinating to the light-green Ag atoms of the 20-atom dodecahedron. FIG. 1F shows six faces of the rhombicuboctahedron are capped with an $Ag_2S$ unit with the bridging S atom tilted off axis, completing the inorganic structure. FIG. 1G shows two Ag atoms (dark green) on each face could be excised from the cluster to create $Ag_4S_5$ capping mount structures, leaving a cubic $Ag_{20}^{2+}$ core. The distance between the two Ag atoms at the bottom of the mount and the nearest Ag atoms of the $Ag_{20}$ core is 2.83 Å, resulting in strong mount-to-core coupling. FIG. 1H shows an alternative $Ag_2S_5$ capping structure can be visualized as a sawhorse-shaped mount that straddles the dark-green Ag atoms of the intact dodecahedral $Ag_{32}$ core. The $Ag_2S_5$ mount is better defined than the $Ag_4S_5$ mount (see FIG. 1G) because its Ag atoms are separated by a larger distance (>3.1 Å) from the nearest atoms of the $Ag_{32}$ core, resulting in a weaker mount-to-core interaction. Color scheme: grey, carbon; orange, oxygen; blue, exterior silver atoms in the mounts; gold, bridging sulfur atoms in the mounts.

FIGS. 6A-6D: Projected densities of states (FIGS. 6B-6D) and orbital images (FIG. 6A) for the $Ag_{44}(SC_6H_5)_{30}^{4-}$ cluster with all atoms at the X-ray determined positions.

FIG. 6B: Different colors correspond to the various angular momentum contributions S, P, D, F, G, H and I, as shown on the right. The Fermi energy $E_F$ is the energy in the middle of the HOMO-LUMO gap, $\Delta_{HL}=0.78$ eV. The inset shows an image of the HOMO one-dimensional superatom orbital superimposed on the structure of the cluster; different colors of the orbital (blue and pink) correspond to different signs of the wavefunction. The 18-electron gap is marked.

FIG. 6C: PDOS of the $Ag_{32}^{14+}$ core, as extracted from the measured structure corresponding to the $Ag_2S_5^{3-}$ mount motif. Selected superatom orbitals are shown at the top of the figure, with the energies and angular momenta marked. The 18-electron gap $\Delta_{HL}=1.29$ eV is noted.

FIG. 6D: PDOS of a $Ag_{20}^{2+}$ core, as extracted from the measured structure, which corresponds to the $Ag_4S^{5-}$ mount motif. Note the absence of an 18-electron gap.

FIG. 7A shows glutathione-capped Ag clusters, with $Ag_{32}(SG)_{19}$ indicated. FIG. 7B shows p-MBA-capped Ag clusters, with three major bands observed. FIG. 7C shows the absorption spectra of the three prominent gel bands, offset for clarity. The spectrum of a $M_4Ag_{44}$ (p-MBA)$_{30}$ solution is shown for comparison (dotted line). The differences can be attributed to an incomplete separation of bands 1 and 2.

FIG. 12: Table 3, displaying sample and crystal data for the $Na_4Ag_{44}(p\text{-}MBA)_{30}$ cluster.

FIG. 13: Table 4, displaying data collection and structure refinement for the $M_4Ag_{44}(p\text{-}MBA)_{30}$ cluster.

FIG. 14: Table 5, displaying atomic coordinates and equivalent isotropic atomic displacement parameters (Å$^2$) for $Ag_{44}$.

FIG. 15: Table 6, displaying bond lengths (Å) for $Ag_{44}$.

FIG. 16: Table 7, displaying bond angles (°) for $Ag_{44}$.

FIG. 17: Table 8, displaying anisotropic atomic displacement parameters (Å$^2$) for $Ag_{44}$.

DETAILED DESCRIPTION OF THE INVENTION

Figure 1A:
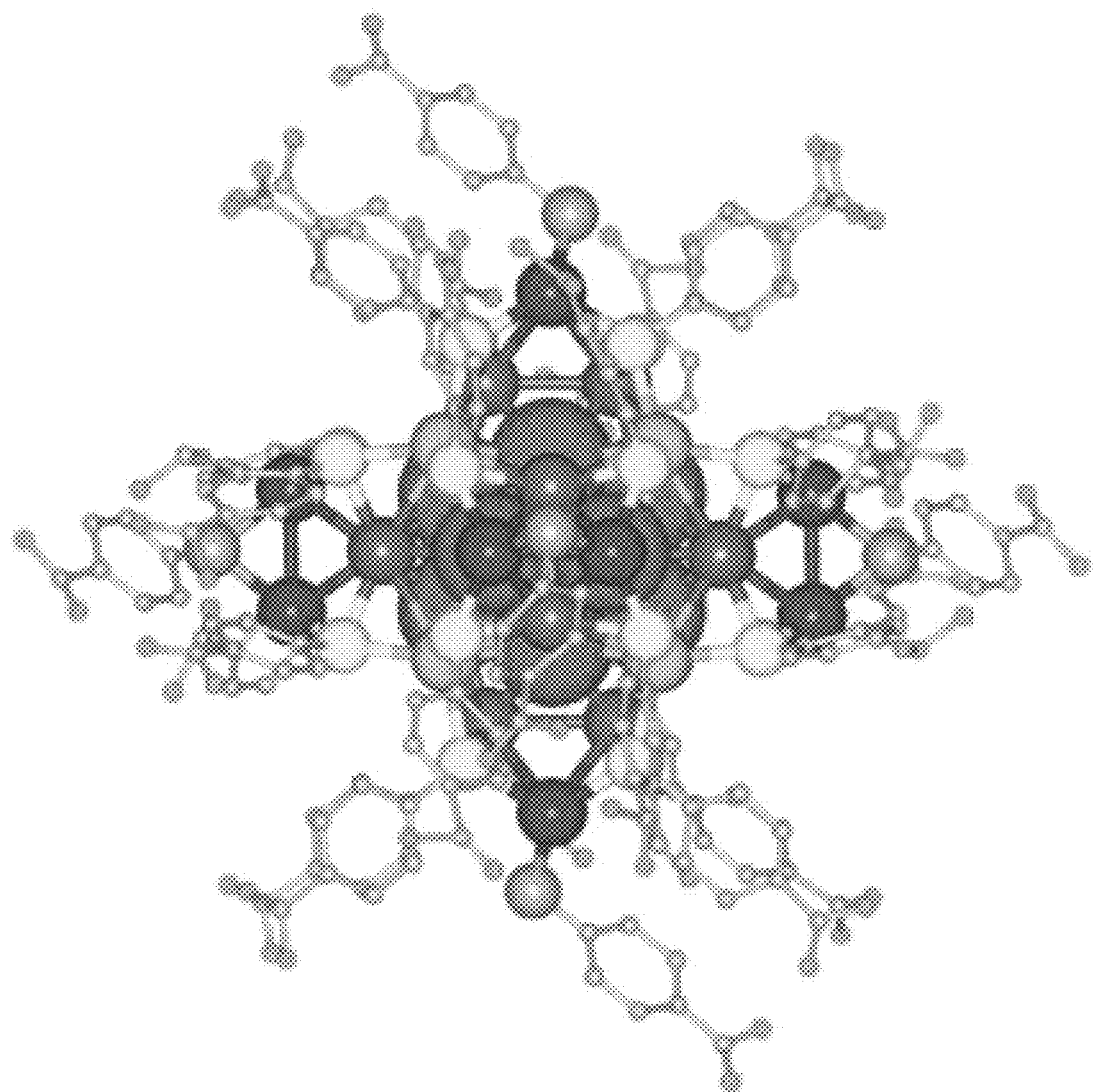
FIGS. 1A-1H: X-ray crystal structure obtained from a $Na_4Ag_{44}(p\text{-}MBA)_{30}$ crystal.
Figure 1B:
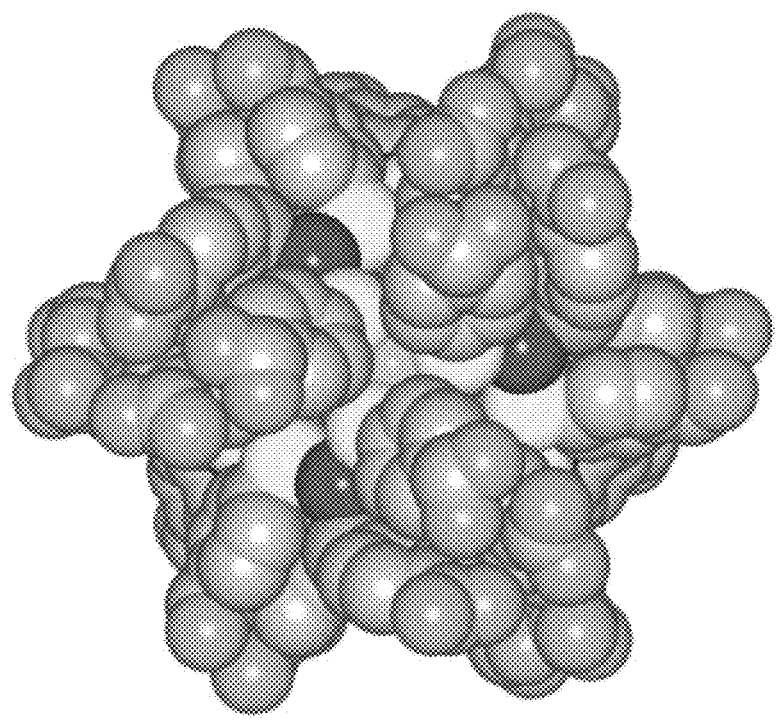
Figure 1C:
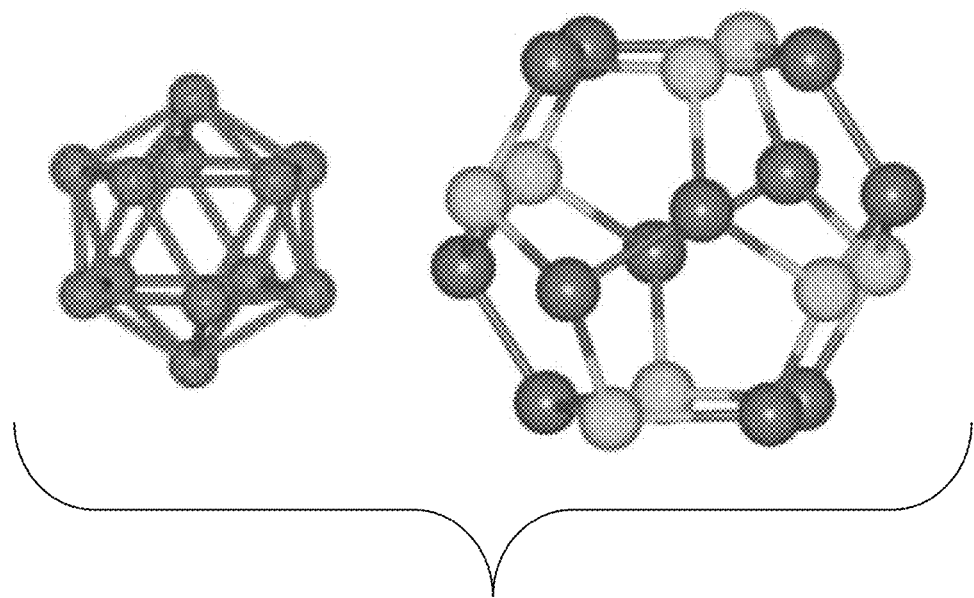
Figure 1D:
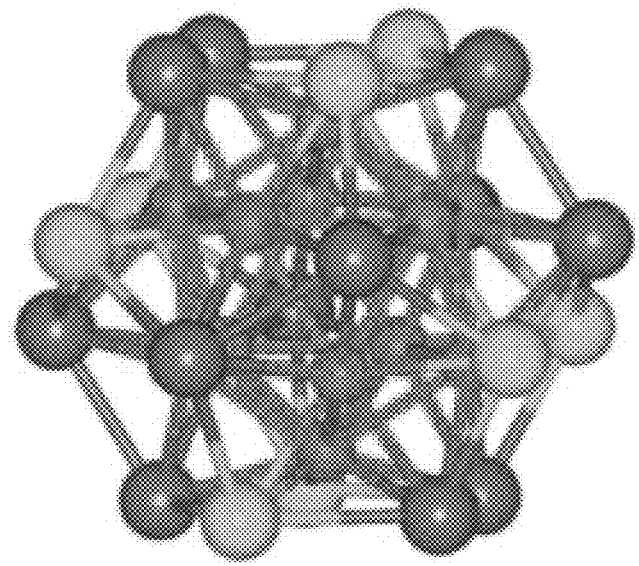
Figure 1E:
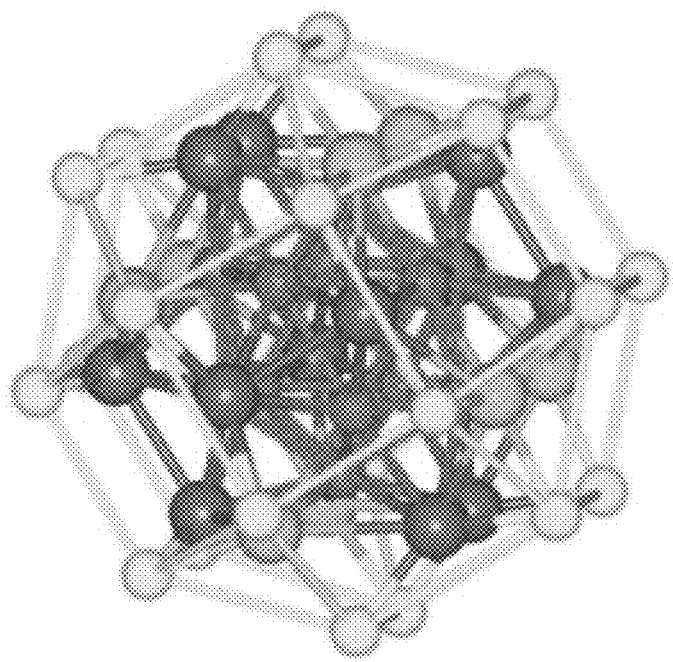

Various embodiments are described herein in the context of $M_4Ag_{44}(SR)_{30}$ and $M_4Ag_{44}(SeR)_{30}$ cluster molecules, methods of making such cluster molecules, and methods of using such cluster molecules. Those of ordinary skill in the art will realize that the following detailed description of the embodiments is illustrative only and not intended to be in any way limiting. Other embodiments will readily suggest themselves to such skilled persons having the benefit of this disclosure. Reference to an "embodiment," "aspect," or "example" herein indicate that the embodiments of the invention so described may include a particular feature, structure, or characteristic, but not every embodiment necessarily includes the particular feature, structure, or characteristic. Further, repeated use of the phrase "in one embodiment" does not necessarily refer to the same embodiment, although it may.

In the interest of clarity, not all of the routine features of the implementations or processes described herein are shown and described. It will, of course, be appreciated that in the development of any such actual implementation, numerous implementation-specific decisions will be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking for those of ordinary skill in the art having the benefit of this disclosure.

Definitions

For convenience, various terms used herein are defined prior to further description of the various embodiments of the present disclosure. Unless otherwise indicated, the terms used herein have the ordinary meaning commonly understood by a person of ordinary skill in the art.

The term "stable" as used herein refers to compounds which possess stability sufficient to allow manufacture and which maintain the integrity of the compound for a sufficient period of time to be detected and preferably for a sufficient period of time to be useful for the purposes detailed herein.

The term "composition" as used herein is intended to encompass a product comprising the specified ingredients in the specified amounts, as well as any product that results, directly or indirectly, from combinations of the specified ingredients in the specified amounts.

Unless stereochemistry is specifically indicated, all stereoisomers of the compounds herein are included, as pure compounds as well as mixtures thereof.

Some of the crystalline forms for the compounds may exist as polymorphs and as such are included. In addition, some of the compounds herein may form solvates with water (i.e., hydrates) or common organic solvents, which are also included.

Protected forms of the compounds herein are further included. A wide variety of protecting groups are possible.

Prodrugs of the compounds herein are included. In general, such prodrugs are functional derivatives of the compounds that are readily convertible in vivo into the required compound.

The term "phosphines" as used herein refers to a group of organophosphorous compounds having the formula $R_3P$, where R is any organic derivative. Non-limiting examples of phosphines include phosphane ($PH_3$); aromatic-containing phosphines, such as phenylphosphine, diphenylphosphine, and triphenyl phosphine; and alkyl-containing phosphines, such as methyl phosphine, diethyl phosphine, ethyl phosphine, dichlorodiphenyl phosphine, dichlorophenyl phosphine, and dimethyphenyl phosphine The term "ethers" as used herein refers to a class of organic compounds having the formula R—O—R', where R and R' are each any organic derivative. Specifically included in the term "ethers" are all polyethers such as, but not limited to, polyethylene glycol.

The term "cosmetic" as used herein refers to any lotion, cream, powder, lipstick, or other preparation for use on skin, hair, or nails, especially including such preparations intended for application to the face.

The term "solvate" refers to a pharmaceutically acceptable solid form of a specified compound containing solvent molecules as part of the crystal structure. A solvate typically retains at least some of the biological effectiveness of such compound. Solvates can have different solubilities, hygroscopicities, stabilities, and other properties. Examples of solvates include, but are not limited to, compounds in combination with water, isopropanol, ethanol, methanol, DMSO, ethyl acetate, acetic acid, or ethanolamine. Solvates are sometimes termed "pseudopolymorphs." The term "hydrate" refers to a solvate with water.

The term "racemate" refers to a mixture that contains an equal amount of enantiomers.

It will be appreciated by one of ordinary skill in the art that asymmetric centers may exist in any of the compounds disclosed herein. Thus, the compounds may be in the form of an individual enantiomer, diastereomer, or geometric isomer, or may be in the form of a mixture of stereoisomers. In certain embodiments, the compounds are enantiopure compounds. In certain other embodiments, mixtures of stereoisomers or diastereomers are provided. Additionally, the compounds encompass both (Z) and (E) double bond isomers (or cis and trans isomers) unless otherwise specifically designated. Thus, compounds generally depicted in structures herein encompass those structures in which double bonds are (Z) or (E).

It will also be appreciated that any of the compounds described herein may be substituted with any number of substituents or functional moieties. In general, the term "substituted" whether preceded by the term "optionally" or not, and substituents contained in formulas, refer to the replacement of hydrogen atoms in a given structure with a specified substituent. When more than one position in any given structure may be substituted with more than one substituent selected from a specified group, the substituent may be either the same or different at every position.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents. For purposes of explanation herein, heteroatoms such as nitrogen may have hydrogen substituents and/or any permissible substituents of organic compounds described herein which satisfy the valencies of the heteroatoms. Furthermore, there is not any intention to be limited in any manner by the permissible substituents.

General Description

In accordance with the present disclosure, stable $M_4Ag_{44}(SR)_{30}$ nanoparticles have been synthesized, where M is a cationic counterion and SR is a mercaptophenyl ligand. The $M_4Ag_{44}(SR)_{30}$ compounds are stable at room temperature, and can be made at near-theoretical yields without the need for size separations. Suitable cationic counterions include any alkali metals (Cs, Na, K, Li, Fr, or Rb), or other cations. Suitable mercaptophenyl ligands include any substituted or unsubstituted ligands having a terminal sulfur and at least one benzene ring. The sulfur atoms can be replaced with selenium such that the cluster molecules contain $M_4Ag_{44}$ $(SeR)_{30}$, where SeR is a substituted or unsubstituted benzenesenol ligand having a terminal selenium and at least one benzene ring. By way of non-limiting examples, suitable mercaptophenyl ligands include, but are not limited to, p-mercaptobenzoic acid (p-MBA), p-mercaptophenyl alcohol, 4-mercaptophenol, or combinations thereof. Suitable benzeneselenol ligands include, but are not limited to, $C_6H_5SeH$. Any of the mercaptophenyl or benzeneselenol ligands can be substituted with substituents such as —OH, —COOH, —$CH_3$, —$NH_2$, —$CH_2OH$, halogens, or combinations thereof. When substituted, the mercaptophenyl ligand or benzeneselenol ligand can have substituents at any one or more of the o-, m-, or p-positions of the benzene ring.

The $M_4Ag_{44}(SR)_{30}$ or $M_4Ag_{44}(SeR)_{30}$ molecules may further comprise coordinating molecules. The coordinating molecules stabilize the clusters and can be exchanged through conventional exchange techniques. The coordinating molecules can be anionic molecules, cationic molecules, neutral molecules, or combinations thereof. Suitable coordinating molecules include the conjugate bases of most acids, or coordinating solvents and molecules. Some non-limiting examples of suitable coordinating molecules include, but are not limited to: deprotonated ethanol (ethoxide) ions, deprotonated methanol (methoxide) ions, hydroxide ions, citrate, acetate, DMSO, DMF, pyridine, $NH_3$, acetone, acetonitrile, ethers, phosphines, or combinations thereof.

The synthesis of the $M_4Ag_{44}(SR)_{30}$ clusters can produce single-sized products with yields around 95%, indicating the clusters are significantly more stable than known species. In addition, the high yield indicates the clusters are formed in a way that is not analogous to typical nanoparticle formation. In other nanoparticle preparations, single-sized products are usually isolated by attrition, wherein less stable sizes are either destroyed or converted into the most stable size. Direct synthesis of a truly single-sized molecular product with yields>95% indicates that these cluster molecules of the present disclosure are more stable than known cluster species. Furthermore, in certain embodiments, the particular size, composition, and stoichiometry of the nanocluster product are immune to changes in experimental parameters such as solvent composition and reactant concentrations.

Synthesis of the $M_4Ag_{44}(SR)_{30}$ clusters relies on particular solvent conditions and stabilizing agents. In a broad aspect, the synthesis is a reduction of a precursor in a water-based solution and in the presence of alkali metal counterions and coordinating ligands. In certain embodiments, the $M_4Ag_{44}(SR)_{30}$ cluster molecules are prepared by a multi-step method that involves the preparation of a Ag(I)—SR precursor, reduction of the Ag(I)—SR precursor to the silver nanoparticle product, and the removal of by-products to isolate the silver nanoparticles. Similarly, synthesis of $M_4Ag_{44}(SeR)_{30}$ clusters involves preparing a Ag(I)—SeR precursor, reducing the Ag(I)—SeR precursor to the silver nanoparticle product, and removing by-products to isolate the silver nanoparticles. In either case, the product can then be protonated and dissolved in diverse solvents. The entire synthesis can be conducted at room temperature, but other temperatures are possible.

The starting materials for the synthesis of $M_4Ag_{44}(SR)_{30}$ molecules are generally silver nitrate ($AgNO_3$) and the mercaptophenyl ligand (SR). For embodiments wherein the final product is a $M_4Ag_{44}(SeR)_{30}$ cluster molecule, benzeneselenol is substituted for the mercaptophenyl ligand. In the non-limiting example where SR is p-MBA, the starting materials are prepared as an insoluble precursor which may be solubilized by increasing the pH, in a homogenous reaction mixture. In this example, the pH is adjusted to about 9 to solubilize the precursor, then further adjusted to about 12 to stabilize the final cluster product. A coordinating solvent is used as part of this step to stabilize the clusters. By way of non-limiting example, the solvent can be a water and ethanol mixture. The pH is raised by the addition of a base. Suitable bases have the formula MOH, $MCH_3CO_2$, or $M_2CO_3$, where M is Li, Na, K, Cs, or $NH_4$. In particular embodiments, the base is selected from CsOH, LiOH, NaOH, KOH, $NH_4OH$, $CsCH_3CO_2$, $CsCO_3$, $LiCH_3CO_2$, $Li_2CO_3$, $NaCH_3CO_2$, $Na_2CO_3$, $KCH_3CO_2$, $K_2CO_3$, $NH_4CH_3CO_2$, or combinations thereof. The rise in pH solubilizes the precursor and allows the solvent to deprotonate and coordinate with the clusters. When aqueous solutions of coordinating solvents such as DMF or DMSO are used, it is not necessary to adjust the pH to stabilize the clusters, although it may be necessary to solubilize the precursor. For embodiments wherein the mercaptophenyl ligand is p-MBA and the pH has been raised sufficiently to fully deprotonate the p-MBA, the following chemical equation illustrates a non-limiting example of the production of the soluble polymeric precursor:

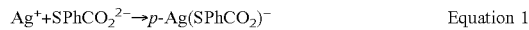
$$Ag^+ + SPhCO_2^{2-} \rightarrow p\text{-}Ag(SPhCO_2)^- \quad \text{Equation 1}$$

Once a homogenous reaction mixture containing the precursor is prepared, the silver in the precursor is reduced by the addition of a reducing agent. The reducing agent can be added dropwise to the reaction mixture. Suitable reducing agents include, but are not limited to, aqueous $NaBH_4$, $LiBH_4$, $KBH_4$, $Al(BH_4)_3$, or combinations thereof. The following chemical equation illustrates a non-limiting example of the reduction of the precursor to the silver nanoparticle product:

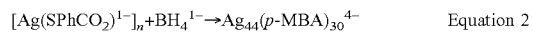
$$[Ag(SPhCO_2)^{1-}]_n + BH_4^{1-} \rightarrow Ag_{44}(p\text{-}MBA)_{30}^{4-} \quad \text{Equation 2}$$

After addition of the reducing agent, the mixture may be stirred for a period of time. In some embodiments, stirring lasts for about one hour. Once stirring is completed, which may be indicated by the appearance of a deep red color in the reaction mixture, the product can be collected by adding a non-solvent, such as DMF in the case of a water-ethanol solvent, to precipitate and separate the product from any leftover materials. Alternatively, precipitation of the product can be achieved by cooling. In the case of $M_4Ag_{44}$(p-MBA)$_{30}$, the product typically contains a non-stoichiometric number of alkali metals. In addition to the four $M^+$ cations, the product may contain $M^+$ cations that serve as counterions to the p-MBA ligands such that the product may be considered the alkali metal salt or conjugate base of the fully acidified cluster.

The solubility of the $M_4Ag_{44}(SR)_{30}$ cluster molecule resulting from this method can be controlled by exchanging coordinating ligands and protonating the cluster such that the $M_4Ag_{44}(SR)_{30}$ molecule may be dissolved in solvents ranging from water to toluene. By way of non-limiting example, the pure solid product can be dissolved in aqueous solution by adding a water-ethanol mixture adjusted to pH 12. It should be noted that particles can be dissolved in water-DMF or water-DMSO solvents without a pH adjustment. Alternatively, the product dissolves readily in acidified DMF or DMSO. Acidification may protonate all of the ligands in the cluster, yielding stoichiometric $M_4Ag_{44}$(p-MBA)$_{30}$ in the case of p-MBA ligands. Adding excess toluene to such solutions causes re-precipitation, but the addition of acidified DMF or acidified DMSO to the toluene yields the toluene solution of the $M_4Ag_{44}(SR)_{30}$ cluster molecule. In this manner, solutions of protic (e.g., water-ethanol), aprotic polar (DMF, DMSO), and nonpolar (e.g., toluene) character are available for subsequent physical and chemical investigations or applications. The skilled practitioner will recognize that many other solvents could be used in place of those provided here by way of examples.

The synthesis method described herein can produce stable, single-sized nanoparticles, relieving the need for separations. The product can be dried and fully redispersed in protic, aprotic, and nonpolar solvents with no loss of material or change in chemical identity. It should be noted that excessive drying should be avoided as this can result in the loss of the protective coordinating ligands, in which case the product may be changed or destroyed. Kilogram-scale production of the $M_4Ag_{44}(SR)_{30}$ compound is possible due to the surprising inertness of these clusters under reaction conditions.

The crystal structure, as determined by X-ray crystallography, of the $M_4Ag_{44}(SR)_{30}$ compound, shown for exemplary purposes in the embodiment where M is Na and SR is p-MBA, is shown in FIGS. 1A-1H. Without wishing to be bound by theory, the crystal structure has exceptionally high symmetry and a compact geometric shape that contributes to cluster stability. The crystal structure comprises a hollow icosahedron ($Ag_{12}$ inner core) within a dodecahedron ($Ag_{20}$ outer core), forming an $Ag_{32}$ excavated-dodecahedral core with icosahedral symmetry. The 20 atoms of the outer core occupy two distinct environments. Eight Ag atoms within the dodecahedral outer core define the vertices of a cube, the faces of which contain the remaining 12 Ag atoms in pairs and are capped in such a way as to create an overall octahedral shape for the particle. Four sulfur atoms from the mercaptophenyl ligands are located on each face of the cube, such that the 24 sulfurs define a slightly distorted rhombicuboctahedron, an Archimedean solid. Each face receives an additional $Ag_2S$ group to complete the inorganic part of the structure and the octahedral shape.

The capping units are complex three-dimensional structures unlike anything seen in gold clusters or in silver thiolate materials. The capping units can be described as $Ag_2S_5$ mounts with four S atoms acting as legs that connect it to the $Ag_{32}$ core. The four S atoms are bridged by a pair of Ag atoms, which, in turn, are bridged by a terminal S atom. Each sawhorse-shaped mount straddles a pair of Ag atoms (dark green in FIGS. 1A-1H) of the intact $Ag_{32}$ core. Altogether, six $Ag_2S_5$ mounts comprise the entire layer protecting the compact, quasi-spherical $Ag_{32}$ core. The two relatively exposed Ag atoms on each side of the six mounts can acquire effective protection from the coordinating solvent, consistent with experimental observations. If this protection is lost, the clusters can polymerize to form larger plasmonic Ag nanoparticles. In this way, the structure is consistent with experimental observations that the cluster is protected by coordinating molecules, such as deprotonated ethanol ions, deprotonated methanol ions, citrate, acetate, DMSO, DMF, pyridine, acetone, $NH_3$, acetonitrile, ethers, phosphines, or combinations thereof. Without wishing to be bound by theory, it is believed that additional coordinating molecules are needed to protect the cluster. If these coordinating molecules are removed, for example by reprotonation of the coordinating ethoxide ions in the case of $M_4Ag_{44}$(p-MBA)$_{30}$.(OEt)$_4$, the clusters become deprotected and polymerize to form larger plasmonic Ag nanoparticles.

Still without wishing to be bound by theory, at least two alternative motifs for the capping-aligand mounts can be constructed, as shown in FIGS. 1A-1H. The cluster can be decomposed into six $Ag_4$(p-MBA)$_5^-$ mount units and a cubic $Ag_{20}^{2+}$ core (FIG. 1G), where the formal charges result from the valences assigned to the silver atoms (1+) and p-MBA ligands (1−). Alternatively, the cluster can be decomposed into six $Ag_2$(p-MBA)$_5^{3-}$ mounts and a quasi-spherical $Ag_{32}^{14+}$ core (FIG. 3H). In both cases, the cluster cores contain 18 Ag 5s electrons. Due to the large HOMO-LUMO gap (FIG. 6C) and a marked degeneracy of the $1D^{10}$ superatom orbitals of the $Ag_{32}^{14+}$ cluster core, as compared to no projected HOMO-LUMO gap for the $Ag_{20}^{2+}$ cluster core (FIG. 6D), the $Ag_2$(p-MBA)$_5$ mounts are the operative capping unit, and $Ag_{32}$ is the core.

The wavefunctions of the cluster molecules exhibit both localized and delocalized character. The localized states are derived from the atomic Ag 4d electrons and are located in the middle of the energy spectrum, whereas the delocalized states are derived from the atomic Ag 5s electrons and can be found near the top and bottom of the electronic spectrum. These delocalized cluster states can be assigned angular momentum symmetries following the electronic cluster shell model, with a superatom Aufbau rule: $1S^2|1P^6|1D^{10}|2S^2|1F^{14}$ . . . . The vertical lines denote shell-closures, which are associated with magic numbers; that is, closed-shell electronic structures are accompanied by the opening of a stabilizing energy gap. The number of electrons not engaged in bonding to sulfur (thiolates) is given by the electron count $n^* = vN_{Ag} - N_L - Z$, where $v=1$ is the valence for $Ag_{44}$(p-MBA)$_{30}^{4-}$, and the electron count is $n^*=18$, which corresponds to the stable superatom with the Aufbau shell filling $1S^2|1P^6|1D^{10}|$.

Figure 1F:
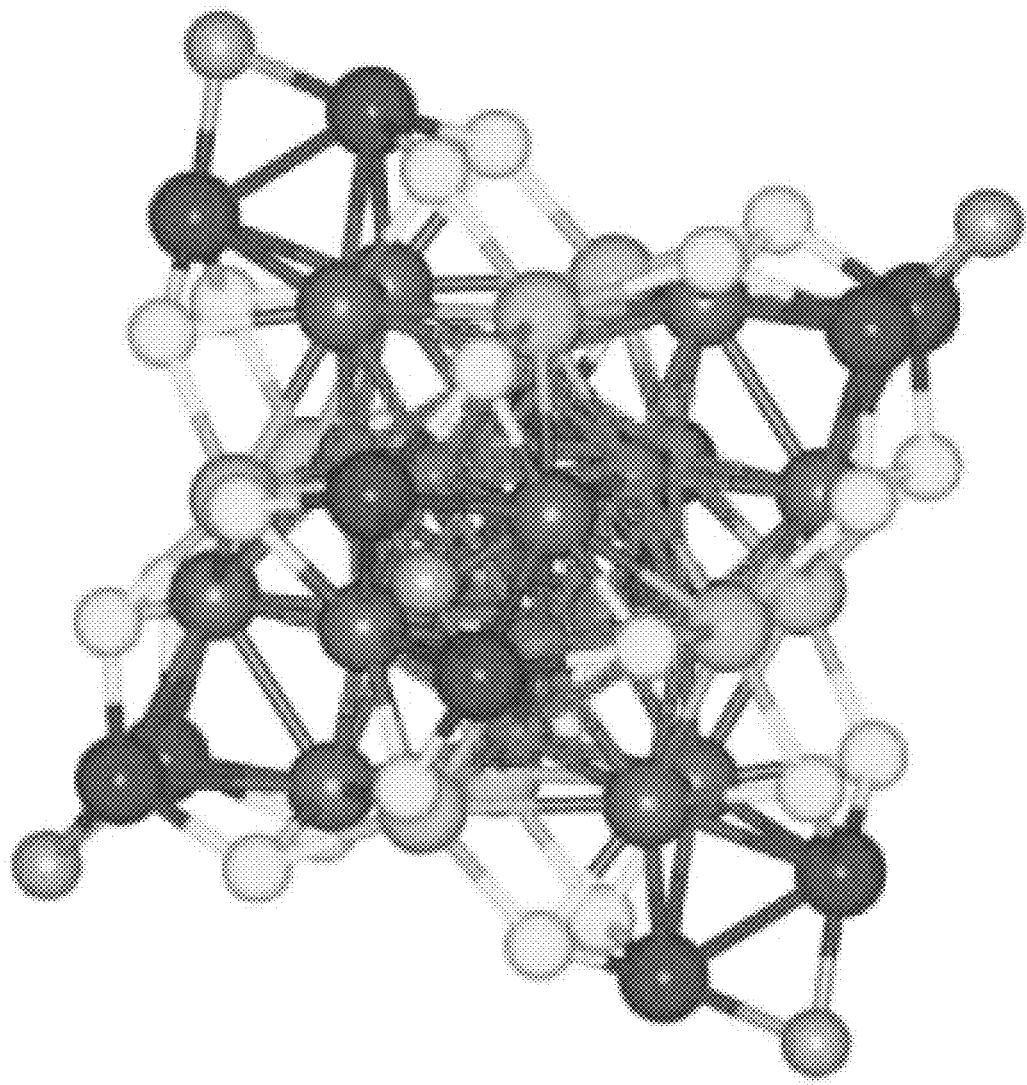
Figure 1G:
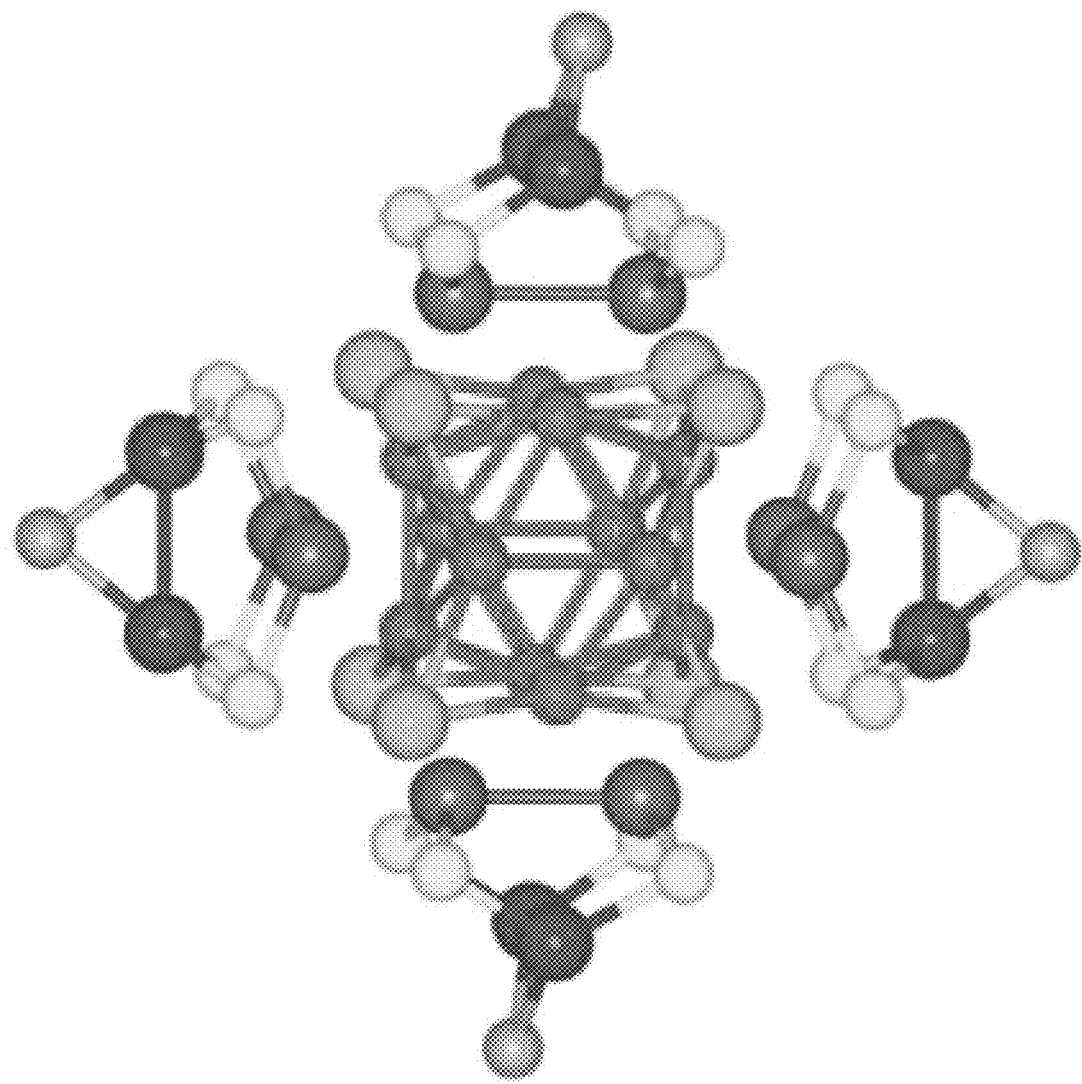
Figure 1H:
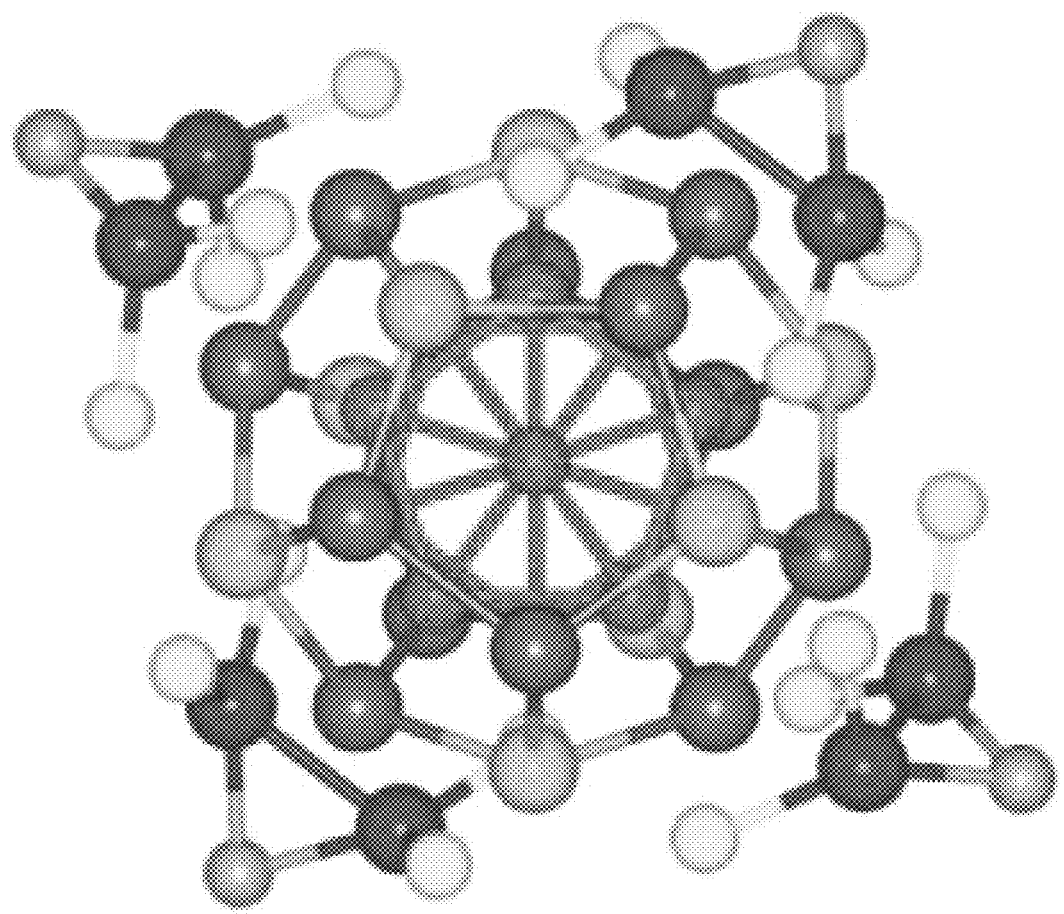

The 18-electron superatom shell-closure and accompanying energy gap stabilization gives a deeper understanding of the structure of the protecting silver-thiolate layer. Two alternative motifs for the aforementioned capping-ligand mounts can be constructed, as shown in FIGS. 1H-1G. The cluster can be decomposed into six $Ag_4$(p-MBA)$_5^-$ mount units and a cubic $Ag_{20}^{2+}$ core (FIG. 1G), where the formal charges result from the valences assigned to the silver atoms (1+) and p-MBA (thiolate) ligands (1−). Alternatively, the cluster can be decomposed into six $Ag_2$(p-MBA)$_5^{3-}$ mounts and a quasi-spherical $Ag_{32}^{14+}$ core (FIG. 1H). In both cases, the cluster cores contain 18 Ag 5s electrons.

Figure 6A:
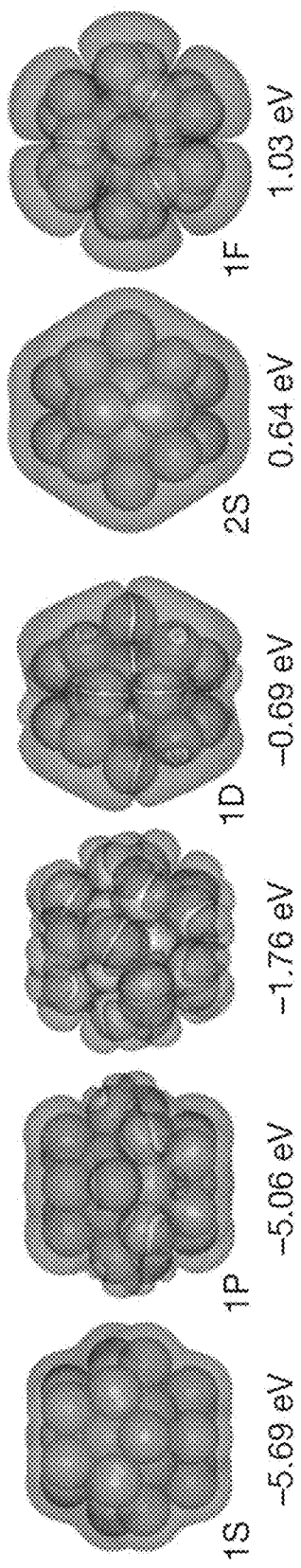

Electronic structure calculations on the two proposed cores, as extracted from the X-ray determined structure, provide a way to differentiate the two competing motifs. The PDOS of the $Ag_{32}^{14+}$ cluster core (FIG. 6C) bears a similarity to that of the entire cluster, including a large HOMO-LUMO gap (FIG. 6B) and a marked degeneracy of the $1D^{10}$ superatom orbitals, reflecting an approximate spherical symmetry of the effective potential governing the motion of the delocalized electrons of the cluster core. (The corresponding superatom orbital shapes are shown in FIG. 6A.) In contrast, similar analysis for the $Ag_{20}^{2+}$ cluster core results in a spectrum that differs considerably from that of the complete particle, and in particular does not exhibit a gap (FIG. 6D), reflecting strong coupling of this core to the $Ag_4$(p-MBA)$_5$ mounts. Therefore, the $Ag_2$(p-MBA)$_5$ mounts are the operative capping unit, and the core comprises $Ag_{32}$.

As described in the examples herein, the long-term stability of the $M_4Ag_{44}$(p-MBA)$_{30}$ clusters was shown to be superior to those of $Au_{25}(SG)_{18}$ clusters, where SG is glutathione. Under both ambient (mildly oxidizing) and reducing conditions, the $M_4Ag_{44}$(p-MBA)$_{30}$ clusters proved to be more noble than the highly stable $Au_{25}$(SG)$_{18}$ cluster. The significant stability of these cluster molecules make them conducive to large-scale production.

It is envisioned that the synthetic method described herein could be practiced in a variety of manners, such as being part of a continuous process to produce clusters at kilogram scales. It is further envisioned that the method described herein could be embodied as parts of a kit or kits. A non-limiting example of such a kit comprises silver nitrate, a mercaptophenyl ligand, and a reducing agent in separate containers, where the containers may or may not be present in a combined configuration. Many other kits are possible, such as kits comprising a soluble precursor mixture in one container and a reducing agent in another container. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive, CD-ROM, or diskette. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

The cluster molecules disclosed herein could be utilized in a wide variety of applications. As one example, the $M_4Ag_{44}$(SR)$_{30}$ compound is useful in cosmetics. Many face creams, soaps, and other cosmetic products currently utilize gold nanoparticles, which can be replaced by the silver nanoparticles of the present disclosure. Nanoparticles have been used as carriers to deliver substances natural substances or synthetic substances) having effects including whitening, sunless tanning, pigment color alteration, anti-aging, treatment of skin diseases (such as acne, seborrhea, and seborrheic dermatitis) or the like, to the skin. The $M_4Ag_{44}$(SR)$_{30}$ compound is useful in any of these cosmetic applications.

As another example, the $M_4Ag_{44}$(SR)$_{30}$ compound could be used as a dye in dye-sensitized solar cells. The $M_4Ag_{44}$(SR)$_{30}$ clusters could be adsorbed onto a $TiO_2$ film to make an electrode for a photovoltaic device. The $M_4Ag_{44}$(SR)$_{30}$ molecules could also be part of a pharmaceutical composition used for drug delivery or other pharmaceutical purposes. For instance, the coordination sites of the core could be linked to molecules that detach inside a body in order to release Ag, a well-known antibiotic, in the body. Similarly, the $M_4Ag_{44}$(SR)$_{30}$ molecules could be used to fabricate anti-bacterial clothing articles because of silver's anti-bacterial or other beneficial properties. The nanoparticles could be homogeneously incorporated into textile fiber so as to provide cosmetic benefits with high effectiveness and durability.

As another example, active pharmaceutical agents or drug molecules could be attached by sulfur or thiol linkages to the coordination sites through an exchange step as described above, and delivered to the body upon detaching from the coordination sites. By way of further non-limiting examples, fluorophores could be attached to the coordination sites for purposes of imaging applications, or carbohydrates could be attached to the clusters for various biological applications. For instance, the $M_4Ag_{44}$(SR)$_{30}$ molecules could be used as labels in immunological measurements, or as photo-fluorescent markers. The thermal stability of the $M_4Ag_{44}$(SR)$_{30}$ molecules enables in vivo applications. Many other uses for the $M_4Ag_{44}$(SR)$_{30}$ compounds are envisioned, such as, but not limited to: electronics, smart windows, electronic panel displays, rewritable electronic papers, screen printing applications, dielectric capacitors, or various articles made from liquid deposition techniques.

Examples

Synthesis

All starting materials were purchased from commercial sources and used without further purification. To generate the precursor, aqueous silver nitrate was combined with ethanolic p-MBA in excess (4 equivalents), and the pH of the mixture was adjusted with CsOH to yield the soluble Ag(I)-pMBA complex in a precursor solution.

Figure 2A:
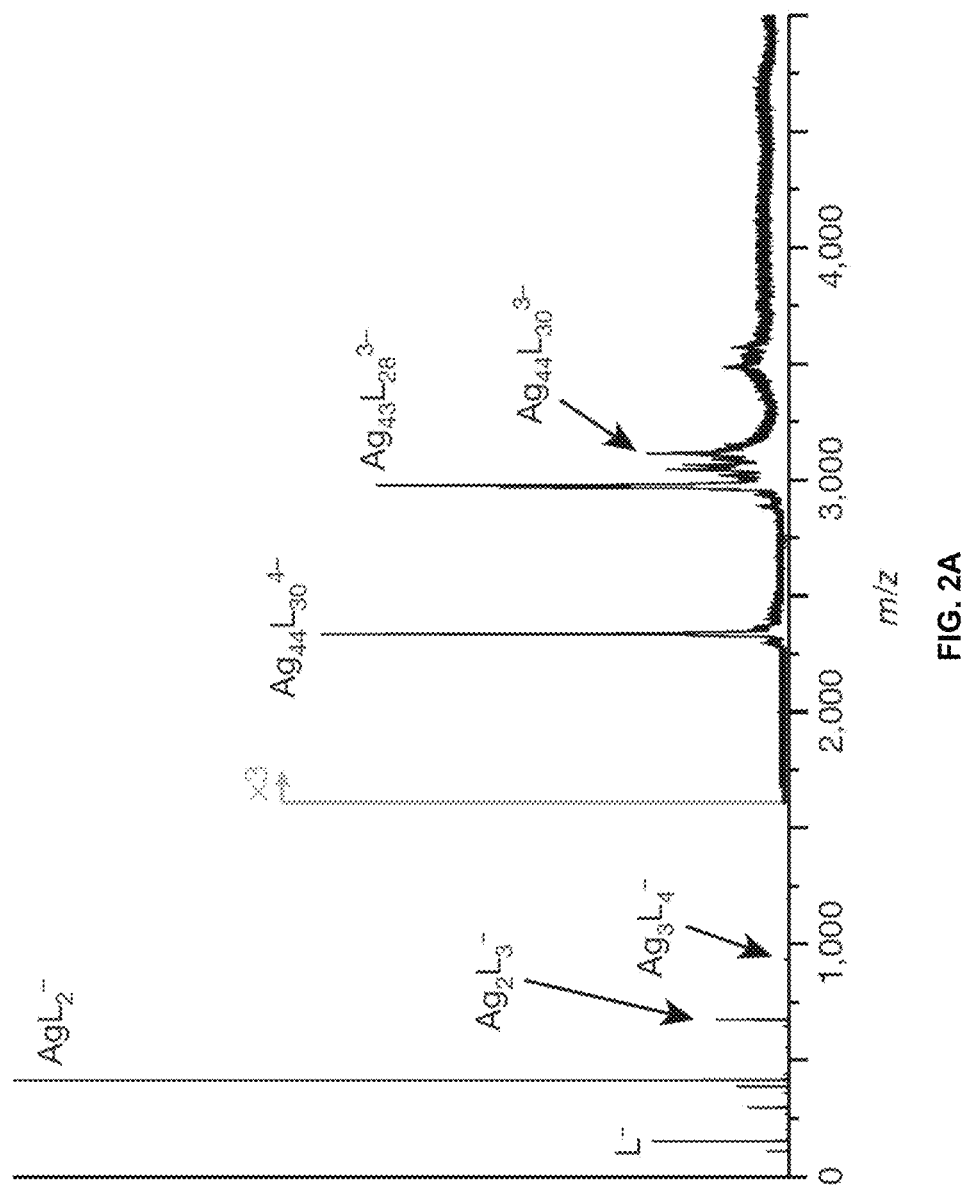
FIG. 2A: ESI-MS spectra of synthesized $M_4Ag_{44}(SR)_{30}$ clusters, showing that only one species is present, and identifying the raw product as $Ag_{44}(p\text{-}MBA)_{30}^{4-}$ with other peaks accounted to different charge states, fragments, and non-specific dimerization. Peaks from 3,000-3,200 m/z are fragments with $3^-$ charge state, and the broad intensity at 3,500 m/z is attributed to non-specific dimerization of fragments with $5^-$ total charge state. Here, L is p-MBA. Elemental analysis identifies four alkali metals that serve as the cationic counterions, giving $M_4Ag_{44}(SR)_{30}$.
Figure 2B:
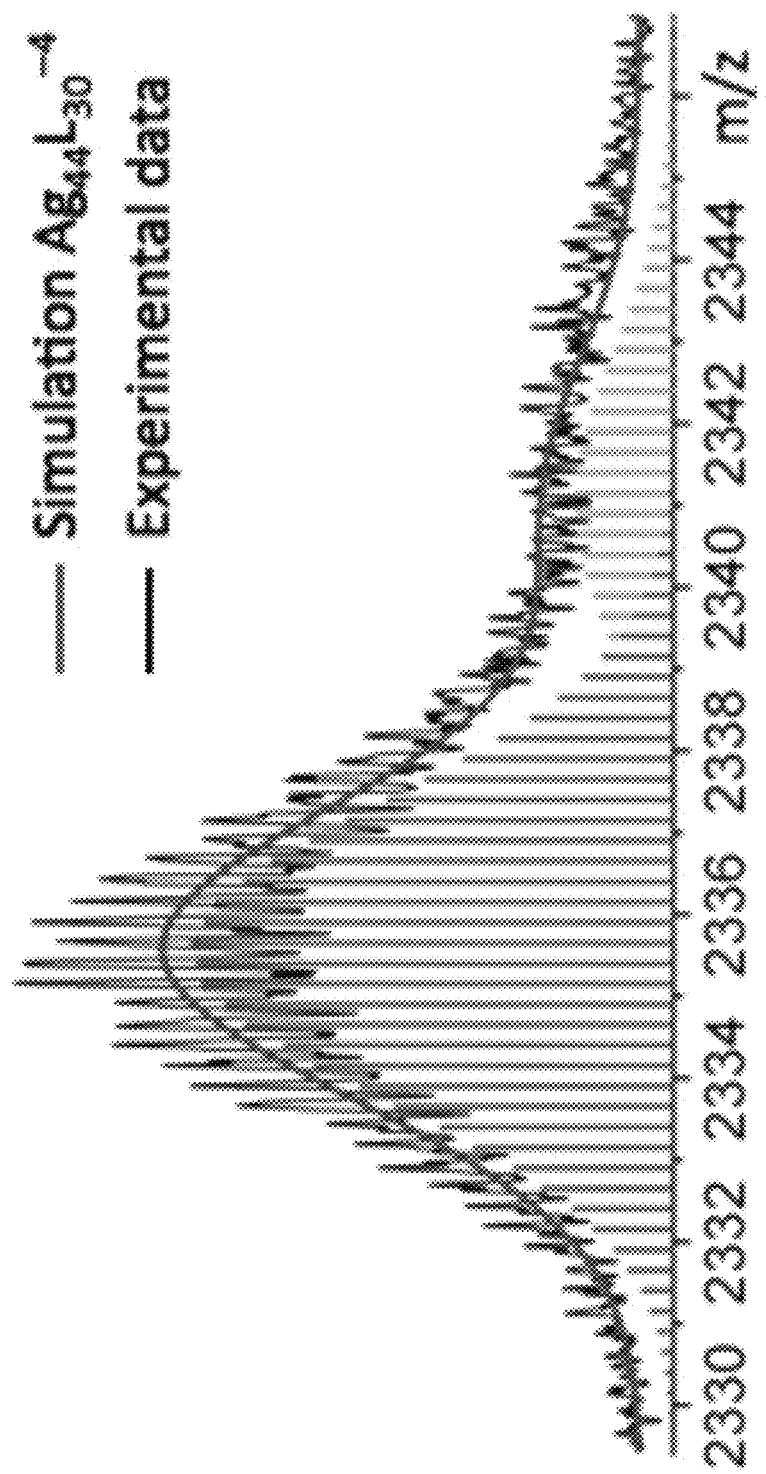
FIG. 2B: The experimental data (black) were fit (blue) using a simulation of the $Ag_{44}L_{30}^{4-}$ ion isotopic distribution (red bars) and that of its Na salt (green bars). Only the heights of each distribution were adjusted during the least-squares fit, which also includes a small vertical offset and accounts for external calibration.

To the precursor solution was added 10 equivalents of $NaBH_4$ dropwise with stirring. Once the addition was completed, the reaction was allowed to incubate for three-quarters of an hour. The initially light yellow solution turned dark yellow, then gray, and finally dark red, then remained unchanged over the succeeding hour. The optical absorption spectrum of this solution agreed quantitatively with that of purified $M_4Ag_{44}$(p-MBA)$_{30}$ complexes. The raw product was positively identified as $Ag_{44}$(p-MBA)$_{30}^{4-}$ by ESI-MS spectroscopy with all four alkali metal counterions identified by elemental analysis, making the molecular formula of the product $M_4Ag_{44}$(p-MBA)$_{30}$. This formula assignment was subsequently confirmed by matching the experimental and theoretical isotopic distributions, as seen in FIG. 2B. The experimental mass spectrum matched the theoretical spectrum for the fully protonated species, indicating the entire 4− charge was carried by the Ag core rather than the carboxylates on the p-MBA ligands. This is consistent with the four alkali counterions determined by elemental analysis and an overall 18-electron configuration. The $Ag_{43}$(p-MBA)$_{28}^{3-}$ complex (m/z 2975) was attributed to electrostatic destabilization and spontaneous fragmentation of $Ag_{44}$(p-MBA)$_{30}^{4-}$ upon desolvation in vacuum. Simply isolating the complex in the mass spectrometer resulted in the spontaneous loss of $AgL_2^-$ to produce $Ag_{43}$(p-MBA)$_{28}^{3-}$ fragments while a small fraction of $Ag_{44}$(p-MBA)$_{30}$ lost only a negative charge. Inducing collisions with the isolated parent ion resulted in the loss of multiple $AgL_2^-$ fragments and the appearance of the $Ag_{42}$(p-MBA)$_{26}^{2-}$ species.

To remove byproducts, the clusters produced were separated from the reaction mixture by precipitation with DMF. Centrifugation removed the precipitated product from the soluble byproducts of the precursor reaction and the reduction reaction, isolating the clusters with a non-stoichiometric number of alkali counterions to the carboxylates on the p-MBA ligands. The carboxylates were fully protonated in DMF by adding acetic acid until the product was fully dissolved, yielding the stoichiometric $M_4Ag_{44}$(p-MBA)$_{30}$ final product. The elemental composition of the product was further determined by inductively-coupled plasma optical emission spectrometry (ICP-OES). This showed the Ag:S:alkali ratio matched the formula (44:30:4) as determined by mass spectrometry. The final product was isolated by precipitating with toluene, a non-solvent, producing a yield greater than 92% by mass of pure solid product. The main losses were attributed to bulk silver and to cleaning and handling, rather than to competing silver clusters or colloids.

Figure 3:
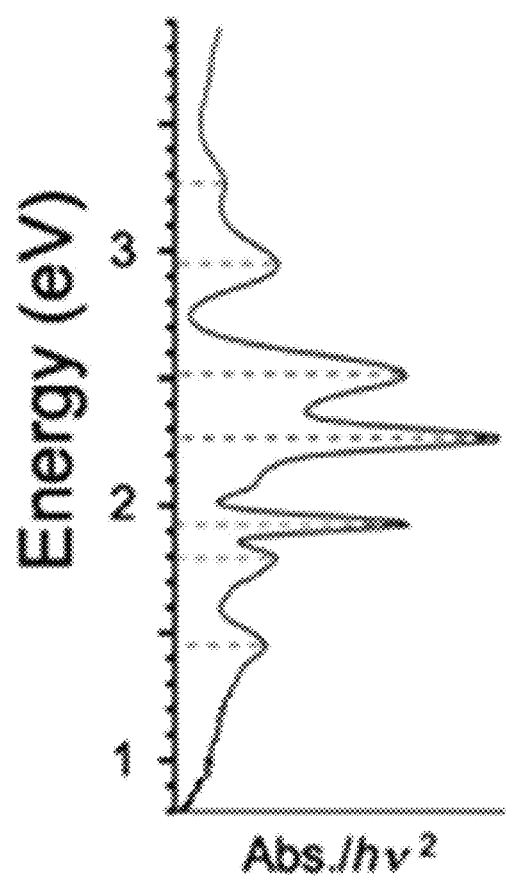
FIG. 3: Scaled absorption spectrum of a $M_4Ag_{44}(p\text{-}MBA)_{30}$ thin film recorded at about 77 K.
Figure 4:
FIG. 4: Photograph of a dish containing about 140 g of $Cs_4Ag_{44}(p\text{-}MBA)_{30}$ clusters that were synthesized using the methods provided by this disclosure. This picture illustrates the large-scale production and ultrastability of $M_4Ag_{44}(SR)_{30}$ compounds made as described herein.

FIG. 3 shows a scaled absorption spectrum of a thin film of $Cs_4Ag_{44}$(p-MBA)$_{30}$ synthesized as described in this example, recorded at about 77 K. FIG. 4 is a picture of about 140 g of $Cs_4Ag_{44}$(p-MBA)$_{30}$ clusters produced from the synthesis described in this example, demonstrating that large-scale production of the material is possible.

Stability Evaluation

Figure 5:
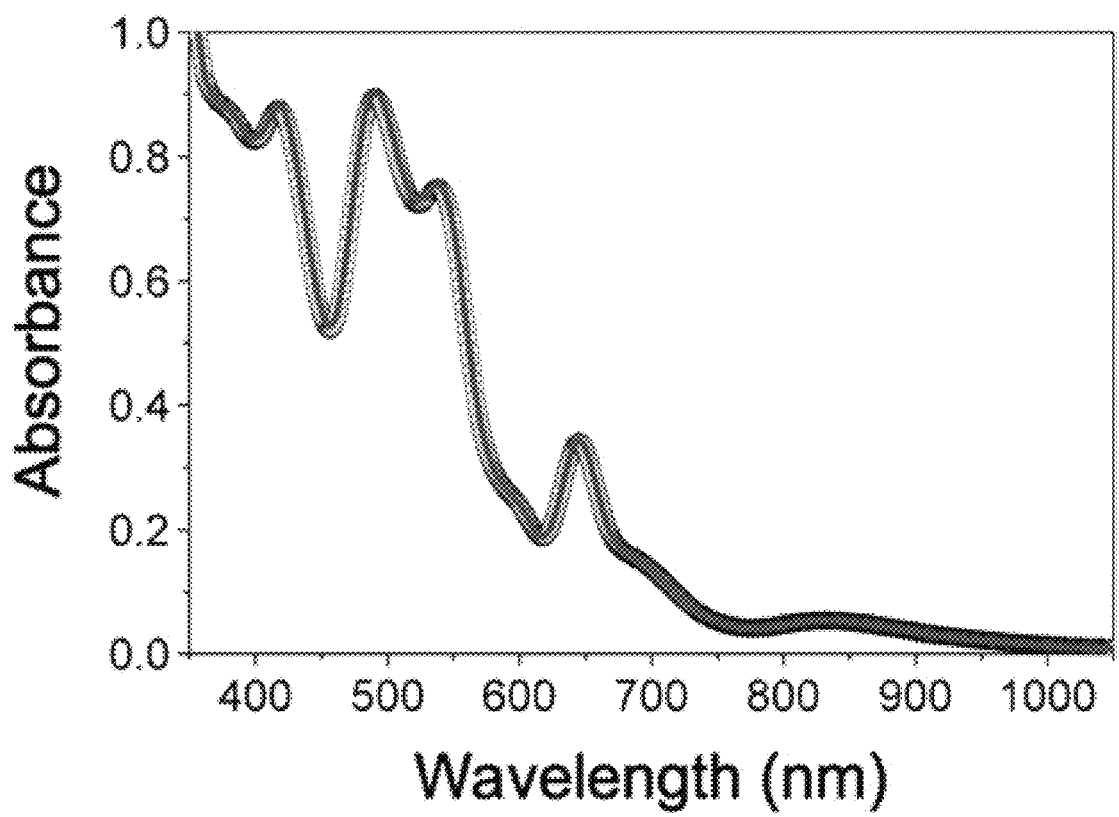
FIG. 5: Absorption spectrum of a $M_4Ag_{44}(p\text{-}MBA)_{30}$ product solution (red line) synthesized in the presence of $M_4Ag_{44}(p\text{-}MBA)_{30}$ "seed" clusters (open circles). This picture illustrates that the clusters, once formed, are inert under reaction conditions.

To test the mechanism of formation, and stability, of the clusters, the synthesis was conducted in the presence of existing $M_4Ag_{44}$(p-MBA)$_{30}$ clusters. Conventional nanoparticle formation would dictate that the existing nanoparticles should act as seeds in this scenario and grow at the expense of nucleating new particles. Instead, $M_4Ag_{44}$(p-MBA)$_{30}$ clusters were formed with identical yields and chemical identity, with or without the existing clusters. Once formed, the clusters were unreactive, behaving as inert molecules instead of as conventional nanoparticles. The absorption spectrum of the $M_4Ag_{44}$(p-MBA)$_{30}$ product solution synthesized in the presence of the "seed" $M_4Ag_{44}$(p-MBA)$_{30}$ clusters is shown in FIG. 5.

An analogous reaction was then conducted wherein $Au_{25}SG_{18}$ clusters were added to a $Au_{25}SG_{18}$ cluster synthesis, where L is glutathione. The $Au_{25}SG_{18}$ clusters were not inert but rather acted as seeds and led to canonical cluster growth upon reduction of the metal salt. The long-term stability of the $Au_{25}SG_{18}$ cluster solutions were also inferior to those of the $M_4Ag_{44}$(p-MBA)$_{30}$ clusters. Under both ambient (mildly oxidizing) and synthetic reaction (reducing) conditions, the $M_4Ag_{44}$(p-MBA)$_{30}$ clusters proved to be more noble than even the exceptionally stable $Au_{25}SG_{18}$ cluster. The inertness of the $M_4Ag_{44}$(p-MBA)$_{30}$ clusters under reducing conditions shows the synthesis of the $M_4Ag_{44}$(p-MBA)$_{30}$ clusters can carry on without regard for existing clusters in the reaction vessel, allowing for large-scale production.

Materials and Methods

Single-crystal x-ray diffraction data were collected for an 80 μm×70 μm×50 μm crystal at 150 K with a Bruker Apex Duo diffractometer (CuKα=1.54178 Å) equipped with an APEX II CCD detector. The structure was solved and refined using the Bruker SHELXTL software package, with space group R-3c. All eight crystallographically independent Ag atoms were obtained by direct methods and all remaining non-hydrogen atoms were located with subsequent difference Fourier techniques. The refinement converged to $R_1$=5.2% with a maximum resolution of 0.83 Å. The highest residual electron density was 1.036e Å$^{-3}$.

The VASP-DFT package was used for computations, with a plane-wave basis, kinetic energy cut-off of 400 eV, PAW pseudopotentials and the PW91 generalized gradient approximation for exchange-correlation. In structural optimizations, convergence was achieved for forces<0.001 eV Å$^{-1}$. Calculations were performed for the X-ray-determined $Ag_{44}(SC_6H_5)_{30}^{4-}$ structure (hydrogens were added and their positions were relaxed, average d(C—H)=1.09 Å).

Projected densities of states (PDOS) were calculated for the $Ag_{44}(SC_6H_5)_{30}^{4-}$ cluster with all atoms at the X-ray-determined positions. These projected densities of states and orbital images are shown in FIGS. 6A-6D. The PDOS for alternative motifs are displayed in FIGS. 6C-6D.

The following reagents were purchased from Fisher Chemical: sodium borohydride, ethanol, methanol, toluene, N,N-dimethylformamide (DMF), dimethyl sulfoxide (DMSO), hydrochloric acid, citric acid, acetic acid, tris base, sodium hydroxide, cesium hydroxide, glycine, acrylamide, bis-acrylamide, tetramethylethylenediamine (TEMED), and tris(hydroxymethyl) amino methane (THAM). Silver nitrate, 4-mercaptobenzoic acid (p-MBA), chloroauric acid, glutathione (GSH), and ammonium acetate were purchased from Sigma-Aldrich. Cetyl trimethylammonium bromide (CTAB) was purchased from Alfa Aesar. Tetraoctylammoniumbromide (TOAB) was purchased from Acros Organics. Ammonium persulfate was purchased from GE Healthcare. All the reagents were used without further purification. De-ionized water (18.2 MΩ cm) was used.

Synthesis of Ag and Au Clusters for Comparison

The silver salt and ligands were combined in a water-ethanol mixture to form the silver-carboxylate precursor, which was a solid at the intrinsic pH. 21 mL of a 11.9 mM aqueous $AgNO_3$ (0.25 mmol) were added to 12 mL of a 83 mM ethanolic solution of p-MBA (1.0 mmol) to form the insoluble precursor. The pH was then raised using aqueous CsOH (50% w/v), first to 9 to solubilize the precursor, then further to 12 to deprotonate the ethanol solvent. The use of CsOH for pH adjustment results in a more stable final product, better solubility, and higher yields.

To the precursor solution, 9 mL of aqueous 278 mM $NaBH_4$ (2.5 mmol) were slowly added dropwise with stirring and allowed to incubate for at least one hour. The initially light yellow solution turned dark yellow, then gray, then dark red upon reduction and remained unchanged over the succeeding hour. The optical absorption spectrum of this deep red solution has a distinct molecular spectrum without any size separations and agrees quantitatively with that of purified $M_4Ag_{44}$(p-MBA)$_{30}$ complexes. (FIG. 5.) The yield was estimated at greater than or equal to 95%, based on the optical density of the solution and the known extinction coefficient.

The product was cleaned first by centrifuging to remove any solids and then by precipitating the clusters with DMF to remove salts and other left-over soluble materials from the reaction. The final product was prepared by dissolving the precipitate into a 1% acetic acid solution in DMF. This process displaced the excess alkali metal atoms by protonating the carboxylates on each p-MBA ligand to produce the stoichiometric $M_4Ag_{44}$(p-MBA)$_{30}$ product, as determined by mass spectrometry and elemental analysis. Here, the 4 alkali metal cations (M) act as counterions to the 4– charge on the cluster core. The ratio of $Na^+$ to $Cs^+$ was determined by EDS. The final product was stable in solution and dry form, could be repeatedly redispersed, and could be easily handled for analysis and characterization. An overall yield of greater than 92% was obtained, as determined by the mass of silver in the $M_4Ag_{44}$(p-MBA)$_{30}$ product after oven drying at 110° C. overnight, which removed any coordinating ligands and allowed accurate mass determined. The loss of the protecting coordinating ligands due to over-drying of the solids renders the material insoluble.

Greater yields are possible. The procedure described above was used to produce 140 g of pure product without any size separations or additional processing with essentially quantitative yield.

Figure 7A:
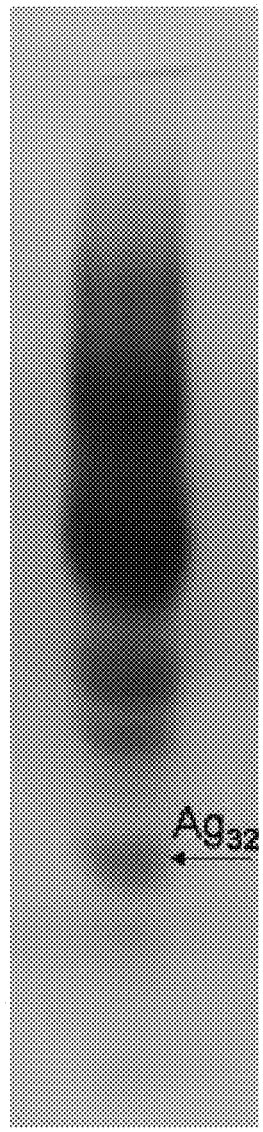
FIGS. 7A-7C: Gel electrophoresis of Ag clusters run on the same gel.

Ag:SG clusters were synthesized. Briefly, aqueous silver nitrate ($5\times10^{-3}$ M) was combined with glutathione ($2\times10^{-2}$ M) to form silver thiolate. This was immediately reduced with 0.2 M sodium borohydride to form Ag:SG clusters. The reaction product was purified by repeated precipitation and washing. Gel electrophoresis was then used to separate the raw product into discrete bands of magic-numbered Ag:SG clusters. The color and abundance of each species varied widely, as shown in FIG. 7A.

Au:SG clusters were synthesized. Briefly, a 50 mL methanolic solution of $HAuCl_4 \cdot 3H_2O$ (0.25 mM) and GSH (1.0 mM) were mixed in a 1:4 ratio. This mixture was cooled to 0° C. in an ice bath for 30 min. Next, an aqueous solution of $NaBH_4$ (0.2 M, 12.5 mL), cooled to 0° C., was added all at once to the above mixture under vigorous stirring. The mixture was allowed to stir for an additional hour to ensure complete reaction. The final product was obtained in the methanol solution as precipitate. This precipitate was centrifuged down, washed with methanol, and dried.

$Au_{25}(SG)_{19}$ clusters were synthesized by etching this crude Au:SG mixture, to enrich the mixture. The Au:SG clusters were dissolved in 50 mL of water along with glutathione (1.0 mM), which was then heated at 55° C. for approximately 6 hours in a water bath. After 6 hours of heating, the solid precipitate was removed from the supernatant and discarded. Methanol was added to precipitate the supernatant, and then the precipitated particles were collected by centrifugation and dried.

Pure $Au_{25}(SG)_{19}$ clusters were separated from the rest of the etched clusters by gel electrophoresis. The etched particles were dissolved in 1 mL of 1% aqueous glycerol solution. This solution was loaded on a 30% home-made PAGE gel. The $Au_{25}(SG)_{19}$ band was extracted from the gel and redissolved into water. Insoluble materials were removed using a 0.22 μm syringe filter, and then the clusters were concentrated to 100 μL with a 3 kDa cutoff filter. Particles were precipitated with ethanol and then centrifuged. The precipitate was dried under vacuum and stored in the freezer.

Characterization of the Clusters

Solution-phase absorption spectra of the clusters were recorded in standard quartz cuvettes using a Nicolet Evolution 300 spectrophotometer. PAGE experiments were run on a Thermo Scientific vertical electrophoresis system (PLODS) using home-made polyacrylamide gels with 20% density and without surfactants.

The aqueous clusters were not stable at normal gel pH, however high pH causes polyacrylamide gels to hydrolyze, therefore an intermediate pH of 10 was chosen. This allowed a large fraction of the clusters to remain unchanged over the course of a gel run. The gel electrolyte and the upper reservoir solution were a mixture of 30% methanol in water with the pH adjusted to 10 using 10 M NaOH. The lower well was filled with the normal tris base and glycine buffer at pH 8.8 to keep the pH of this solution constant. Each lane was loaded with 20 μL of a cluster solution with a concentration of 30 mg/mL, using a water-methanol solvent adjusted to pH 12. Ag glutathione clusters were run in separate lanes for comparison. The gels were run at 300 V for 16 hours.

Figure 7B:
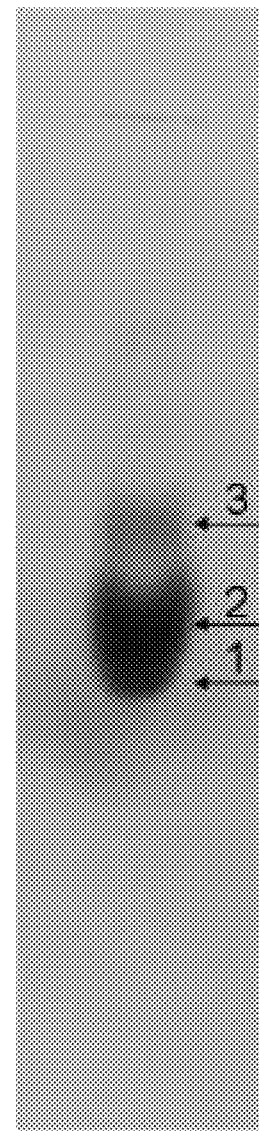
Figure 7C:
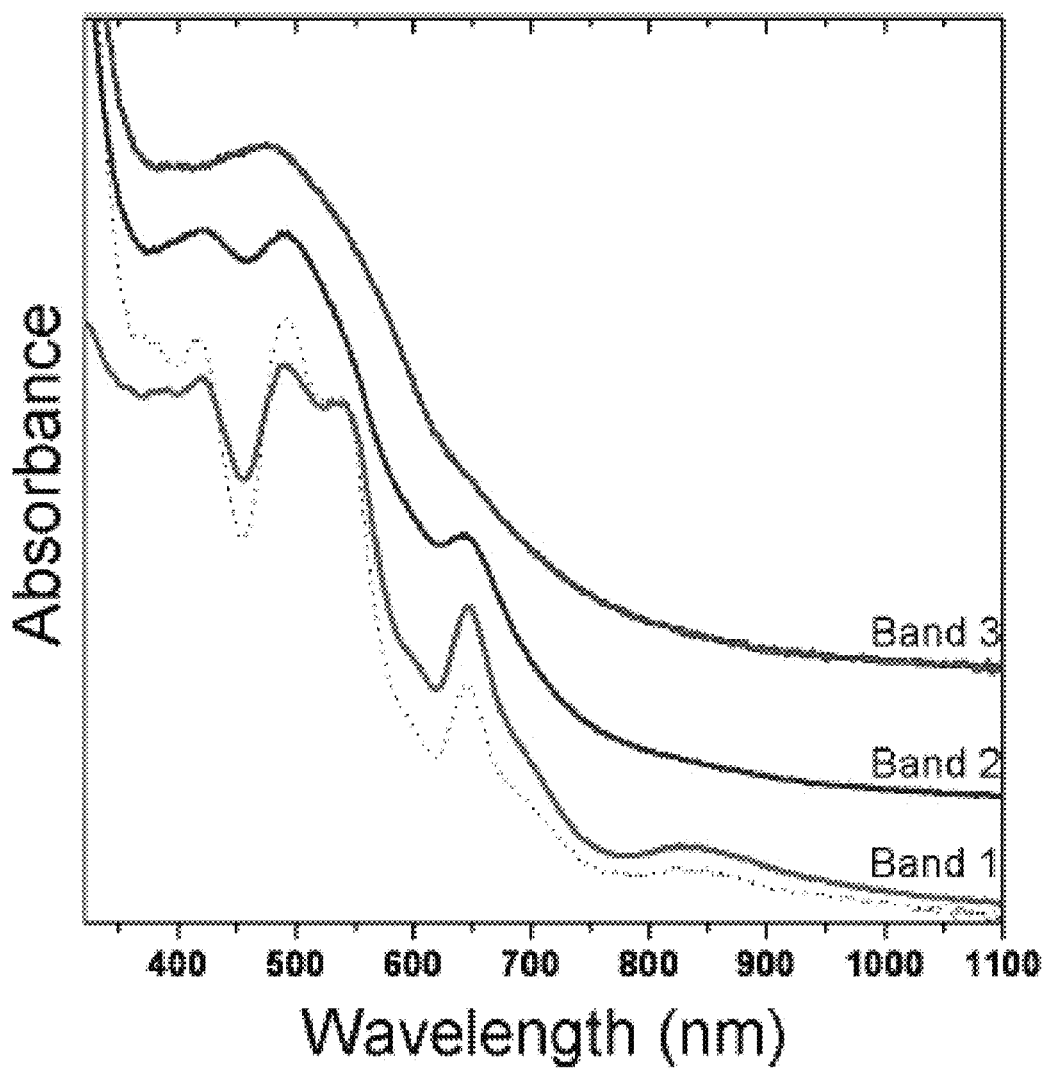

Four bands appeared in each Ag:p-MBA cluster lane, as shown in FIG. 7B. UV-Vis measurements showed that the lower band corresponded to $M_4Ag_{44}(p\text{-}MBA)_{30}$ clusters and the higher bands had different spectra (FIG. 7C), indicating different chemical species. It is clear from the spectra that these species were not present in the as-synthesized product, but rather appeared due to the instability of the clusters at the lower pH conditions needed to run the gel. The highest band (with the largest clusters) resembled the plasmonic Ag nanoparticles that are produced from $M_4Ag_{44}(p\text{-}MBA)_{30}$ clusters when they are destabilized by dissolving them in water-methanol solutions at pH 10. Only some of the as-synthesized $M_4Ag_{44}(p\text{-}MBA)_{30}$ clusters survived and ran as a single band. This was also true with the Ag glutathione particles (FIG. 7A), which ran with fewer bands than expected for a more neutral pH.

Ag:pMBA clusters were dissolved in DMF and diluted in the same solvent to a concentration of approximately 0.5 mg/mL. All mass spectrometry data were collected on a Synapt HDMS quadrupole time-of-flight ion mobility mass spectrometer equipped with a nanospray source (Waters Corp.), operated in negative ionization mode, and using home-made continuous-flow fused silica emitters. Instrumental parameters were maintained at the following values unless otherwise indicated: capillary voltage, 1.8-3.0 kV; sampling cone, 15 V; extraction cone, 2.7V; cone gas flow rate, 45 L/h; trap collision energy, 0.5 eV; transfer collision energy, 1.0 eV; source temperature, 40° C.; and desolvation temperature, 120° C. External calibration was performed in positive ionization mode in the range of $100 \leq m/z \leq 5000$ using a solution of sodium cesium iodide. All mass spectra were averages of 300 scans and collected in V-mode except for the FIG. 2B, which was an average of 3500 scans and collected in W-mode for increased resolution and the detection of isotopic distribution. Mass spectra were processed using Masslynx 4.1 software (Waters Corp.). Isotopic distributions were simulated using the freeware, mMass, version 4.0.

For tandem mass spectrometry (MS/MS), all instrumental parameters were maintained at the values listed above except for the trap collision energy, for which mass spectra were recorded at 0.5, 6.0, and 15.0 eV. Tandem mass spectra recorded at trap CE of 0.5 eV represent only precursor ion selection without any increase in CE over the value used for mass measurement (MS1).

Figure 2C:
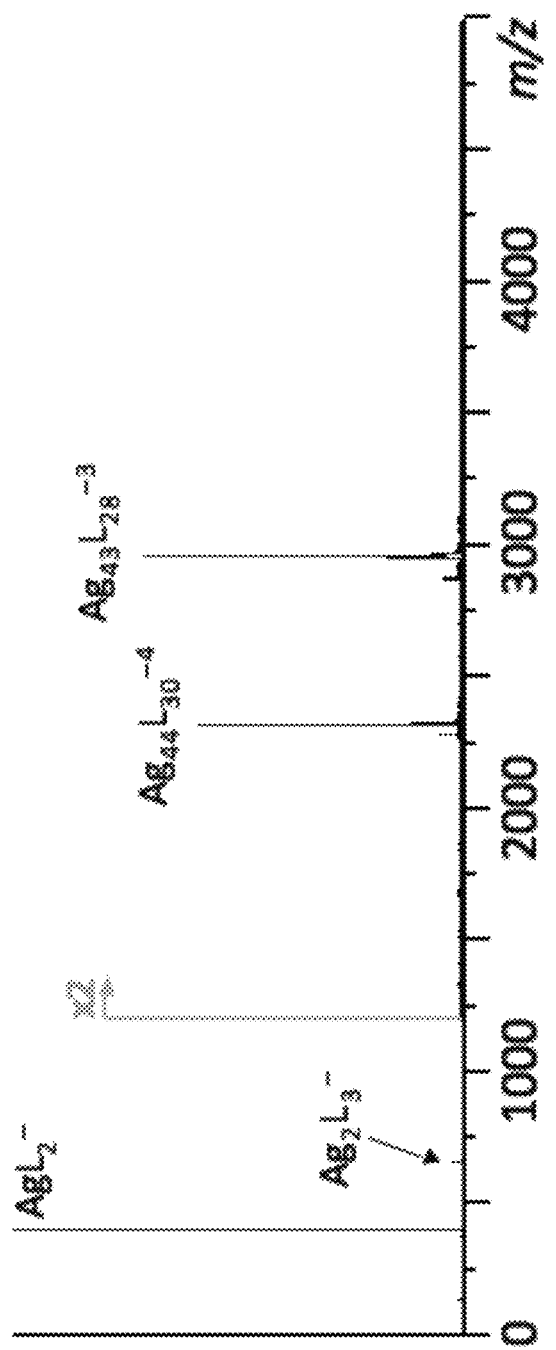
FIG. 2C: Isolated $Ag_{44}L_{30}^{4-}$ ions spontaneously fragment into $Ag_{43}L_{28}^{3-}$ and $AgL_2^-$ when desolvated, where L is p-MBA.

ESI-MS of the raw product identified several ion species that were all attributed to a single cluster size. The parent species (m/z 2336) was identified as $Ag_{44}(p\text{-}MBA)_{30}^{4-}$. (FIG. 2A.) This chemical formula assignment was confirmed by matching the experimental and theoretical isotopic distributions. (FIG. 2B.) The experimental data only matched the simulated isotopic distribution for the fully protonated species, therefore the entire 4− charge was carried by the Ag core rather than by the carboxylates on the p-MBA ligands. This is consistent with the four alkali counterions determined by the elemental analysis and an overall 18-electron configuration. The higher mass peak in FIG. 2B (green bars) is due to a sodium salt of the cluster, in which one carboxyl proton was replaced by one $Na^+$ ion per cluster. The $Ag_{43}(p\text{-}MBA)_{28}^{3-}$ complex (m/z 2975) was attributed to electrostatic destabilization and spontaneous fragmentation of $Ag_{44}(p\text{-}MBA)_{30}^{4-}$ upon desolvation. (FIG. 2C.)

Figure 8:
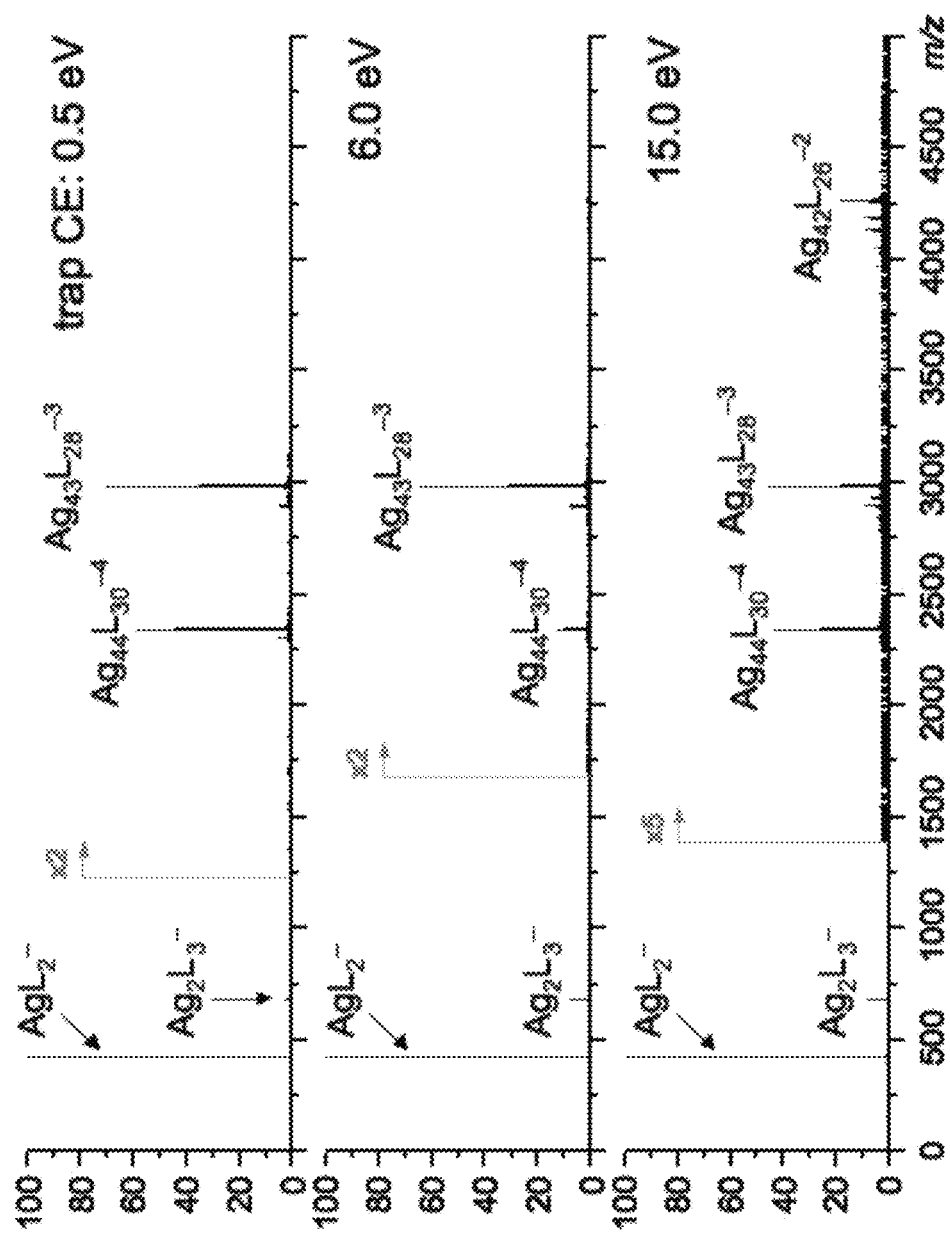
FIG. 8: Tandem mass spectrometry of $Ag_{44}L_{30}^{4-}$ ions. Once mass selected, fragmentation of the ions was observed for different trap collision energies, as noted.

Simply isolating the $Ag_{44}(p\text{-}MBA)_{30}^{4-}$ complex in the mass spectrometer resulted in the spontaneous loss of $AgL_2^-$ to produce $Ag_{43}(p\text{-}MBA)_{28}^{3-}$ fragments while a small fraction of $Ag_{44}(p\text{-}MBA)_{30}$ lost only a negative charge. Inducing collisions with the isolated parent ion resulted in the loss of multiple $AgL_2^-$ fragments and the appearance of the $Ag_{42}(p\text{-}MBA)_{26}^{2-}$ species (FIG. 8).

Elemental Analysis

The counterions for the clusters were determined by elemental analysis. Inductively-coupled plasma optical emission spectrometry (ICP-OES) and energy dispersive x-ray spectroscopy (EDS) were used to find the atomic ratios. The ICP-OES (IRIS Intrepid II, Thermo Electron Corp.) was operated with a flush and analysis pump rate of 130 rpm, RF power of 1150 W, nebulizer pressure of 32.1 psi, and auxiliary gas flow rate of 1.0 L/min. Two sets of samples were prepared, one using NaOH and $NaBH_4$, and the other using KOH and $KBH_4$. Once synthesized, both sets of samples were protonated and precipitated twice, then cleaned by precipitation one additional time. The precipitate was then dissolved in water, digested with nitric acid, and injected into the ICP-OES. For the sodium sample, the Ag:S ratio was 1.5:1, as expected for a $Ag_{44}L_{30}$ cluster. The Ag:Na ratio was 10.6:1, which implies 4.2 $Na^+$ ions per cluster. For the potassium sample, the Ag:S ratio was 1.6:1, very close to the expected value for a $Ag_{44}L_{30}$ cluster. The Ag:K ratio was 10.2:1, which implies 4.3 $K^+$ ions per cluster. Both of these results are consistent with four alkali metal counter ions for the $Ag_{44}L_{30}^{4-}$ ion and a molecular formula of $M_4Ag_{44}(p\text{-}MBA)_{30}$.

EDS spectra were recorded using a Bruker Quantax EDS system, which was part of a JOEL JSM-7500F 30 keV cold-cathode field-emission scanning electron microscopy system. Samples for EDS were prepared by drying dispersions of the precipitates onto Si substrates. Substrates were mounted onto Al sample stubs using carbon tape. Spectra showed a 3:2 ratio of Ag:S, also confirming the molecular formula of $M_4Ag_{44}(p\text{-}MBA)_{30}$.

Comparison of Gold-Thiolate and Silver-Thiolate Cluster Nobility

The tendency of Au and Ag clusters to react and form other species was evaluated under strongly reducing (synthetic) and mildly oxidizing (ambient) conditions. The $M_4Ag_{44}(p\text{-}MBA)_{30}$ clusters were compared to $Au_{25}SG_{18}$ since they are the most stable Au clusters in this size range that are water soluble, which allowed them to be analyzed by gel electrophoresis. The best comparison would use the same p-MBA ligands, but $Au_{25}(p\text{-}MBA)_{18}$ was found to be too unstable for this stability evaluation. Although $Au_{25}$(captopril)$_{18}$ was reported to be more stable than $Au_{25}SG_{18}$ at 80° C., it was found to be unsuitable for room temperature studies as about ⅔ of the $Au_{25}$(captopril)$_{18}$ clusters decayed after only 12 hours compared to about 10% of the $Au_{25}SG_{18}$.

To compare reactivity of the clusters during synthesis, $M_4Ag_{44}(p\text{-}MBA)_{30}$ clusters and $Au_{25}SG_{18}$ clusters were added to the Ag and Au precursor solutions before the reduction step (also referred to herein as seeding). The reaction mixtures were then reduced. In the case of $M_4Ag_{44}(p\text{-}MBA)_{30}$, none of the seed clusters participated in the reaction and remained completely inert. A reaction mixture was prepared and split into two halves. The first half was reduced to form clusters. Once the reaction was complete, this cluster solution was recombined with the second half. The resulting mixture of clusters and precursor was then reduced to form a final cluster solution. The concentration of this final solution was identical to that of the first half, meaning that the clusters synthesized in the first reaction did not affect the results of the second reaction. The structure of the spectra was also identical (see FIG. 5), indicating that there was no change in the chemical identity of the clusters from either the first or second reaction. The clusters did not change, nor did they affect the final product's identity and yield. This shows that under reductive conditions, the $M_4Ag_{44}(p\text{-}MBA)_{30}$ clusters were inert.

Figure 9A:
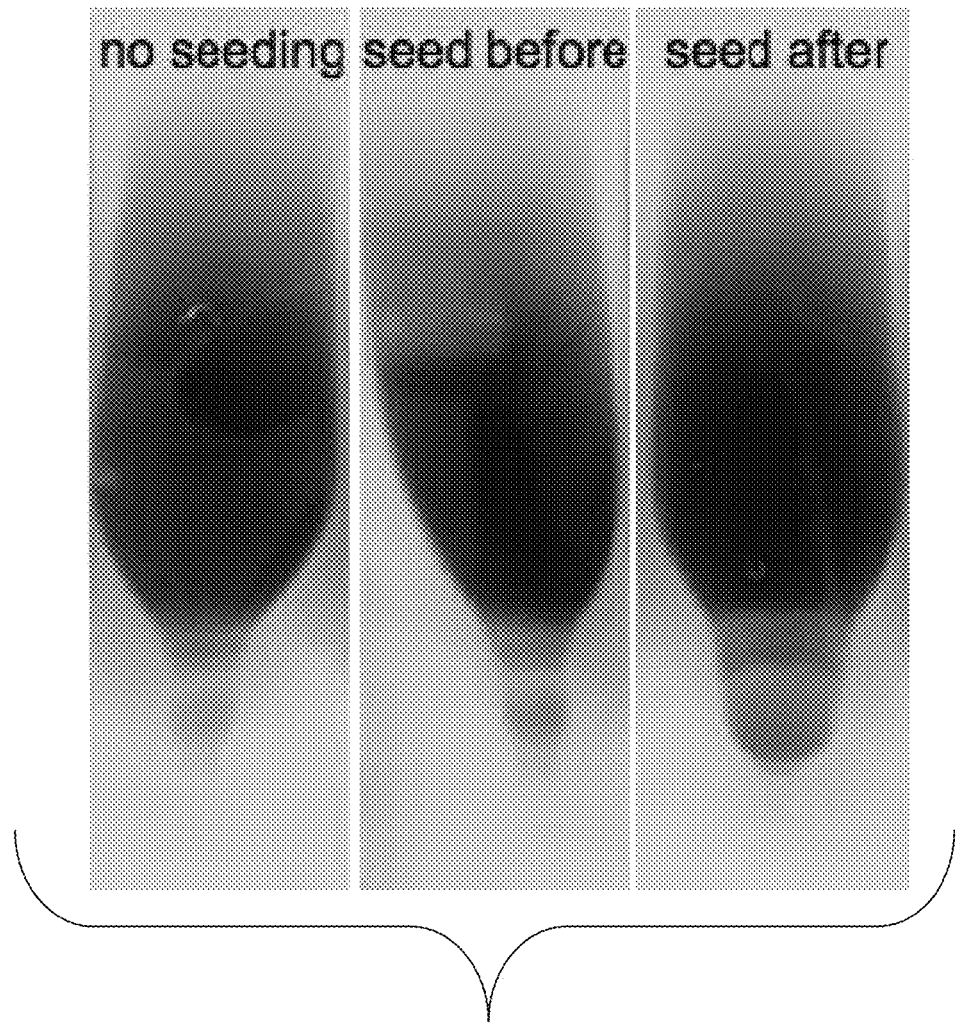
FIG. 9A: Gel electrophoresis of Au:SG clusters synthesized with and without $Au_{25}SG_{18}$ cluster seeds. Synthesis with seeds (middle) shows that the $Au_{25}SG_{18}$ clusters reacted to form larger clusters. Adding seeds after the synthesis shows the result expected if the $Au_{25}SG_{18}$ clusters had been inert.

In the case of $Au_{25}SG_{18}$, all of the seed clusters participated in the reaction. A solution of $Au_{25}SG_{18}$ clusters was prepared separately and added to a Au:SG precursor solution. When the precursor was reduced in the presence of the pre-made $Au_{25}SG_{18}$ clusters, little of the $Au_{25}SG_{18}$ seed material remained, as seen in FIG. 9A. The final mass distribution looked similar to the mass distribution of an unseeded reaction, but with slightly more high-mass clusters. This indicated that the seed clusters grew, as would be expected for typical nanoparticle syntheses. This is in contrast to a solution with $Au_{25}SG_{18}$ seeds added after the reduction step, as seen in FIG. 9A. This shows that under reactive conditions, the $Au_{25}SG_{18}$ clusters were reactive.

Figure 9B:
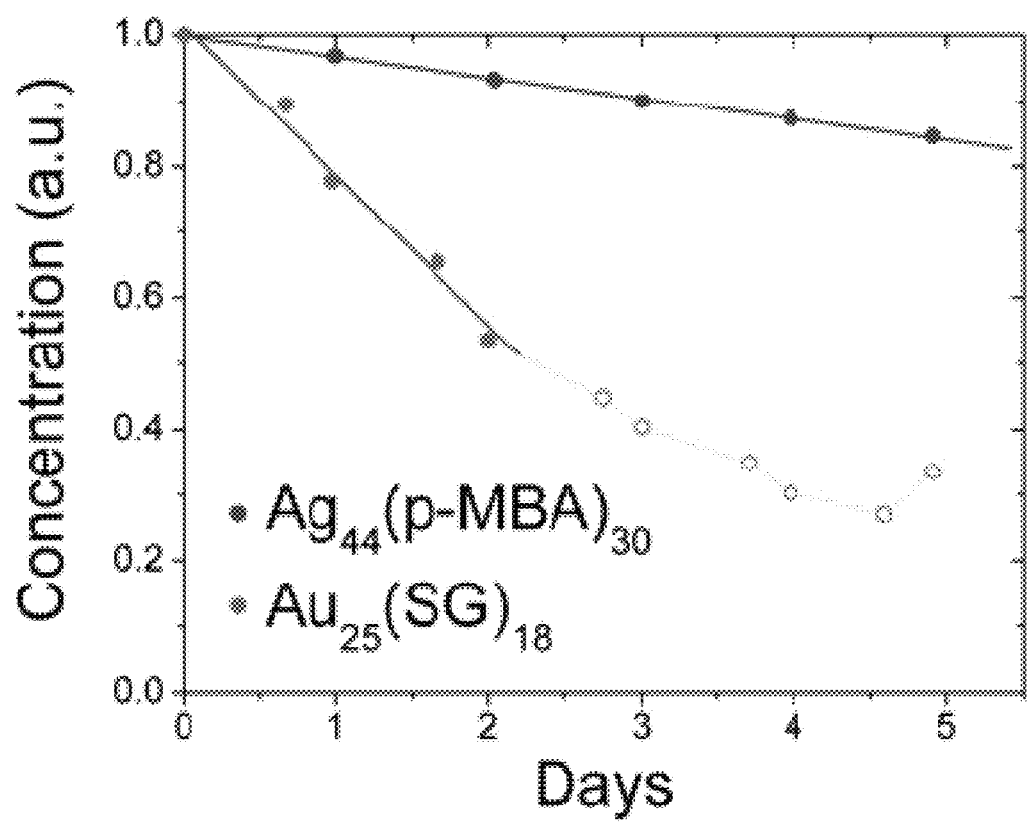
FIG. 9B: Comparison of $M_4Ag_{44}(p\text{-}MBA)_{30}$ and $Au_{25}SG_{18}$ solution ambient stability, with linear fits shown in red. Open symbols for Au indicate that the spectra contain other species, making the measured concentrations higher than expected and therefore unacceptable for decay rate measurements. Notably, the apparent concentration increased on day 5.

To compare the long-term stability of the clusters under ambient (mildly oxidizing) conditions, solutions of $M_4Ag_{44}$ (p-MBA)$_{30}$ and $Au_{25}SG_{18}$ clusters were prepared and aged. Their stability was monitored by tracking their concentrations as a function of time, as shown in FIG. 9B. Solutions of $M_4Ag_{44}(p\text{-}MBA)_{30}$ were prepared in DMSO with ammonium acetate (a coordinating ligand) and solutions of $Au_{25}SG_{18}$ clusters were prepared in water. Concentrations of each were similar, based on known extinction coefficients.

The concentrations of the $Au_{25}SG_{18}$ clusters decayed relatively rapidly, such that there was a visible change in the solutions in just days. The solutions changed color over time, accompanied by an evolution of the spectrum, indicating that other cluster species were produced over time. In this case, solutions were deemed sufficiently free of other species for fitting and further analysis for only the first two days. In contrast, the $M_4Ag_{44}(p\text{-}MBA)_{30}$ clusters decayed more slowly and maintained the same color and spectrum over time. Only silver thiolates were produced as the particles decayed, meaning other species were formed. Therefore, the linear decrease in concentration with time is interpreted solely as a decay of $M_4Ag_{44}(p\text{-}MBA)_{30}$ clusters for the entire extent of the measurements. A comparison of the decay rates showed that the $Au_{25}SG_{18}$ clusters decayed 7 times faster than the $M_4Ag_{44}(p\text{-}MBA)_{30}$ clusters. Cluster solutions that were undisturbed decayed even more slowly than those in FIG. 9B.

Crystallization of Ag Clusters

Figure 10A:
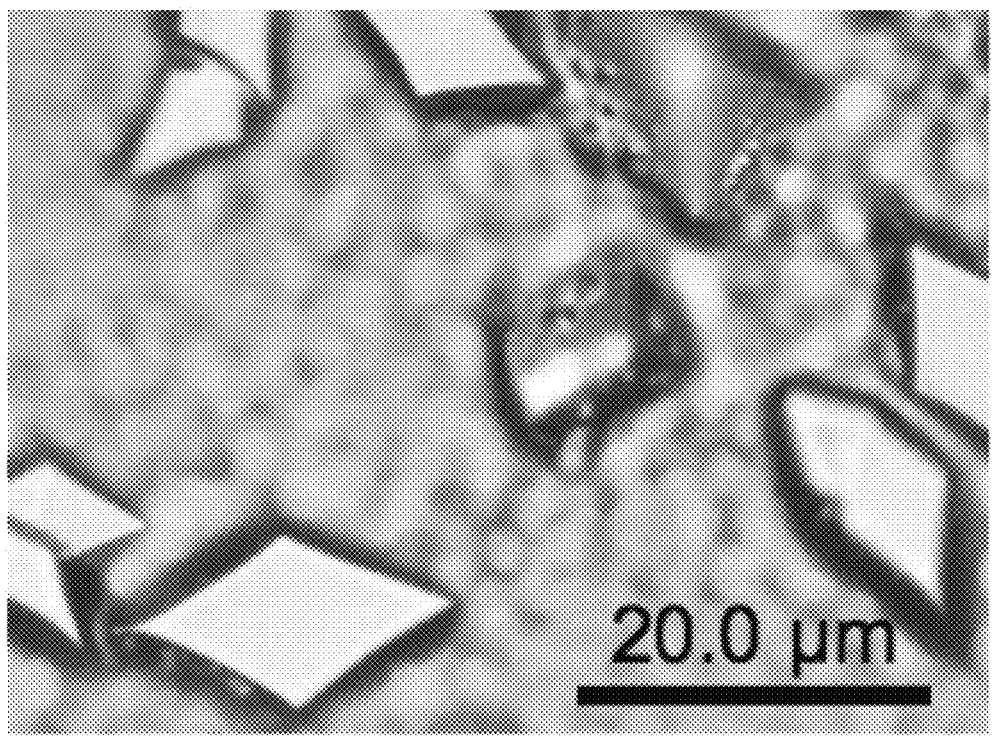
FIGS. 10A-10B: Optical micrographs of typical crystals of $M_4Ag_{44}(p\text{-}MBA)_{30}$ clusters using episcopic (FIG. 10A) and diascopic (FIG. 10B) illumination.
Figure 10B:
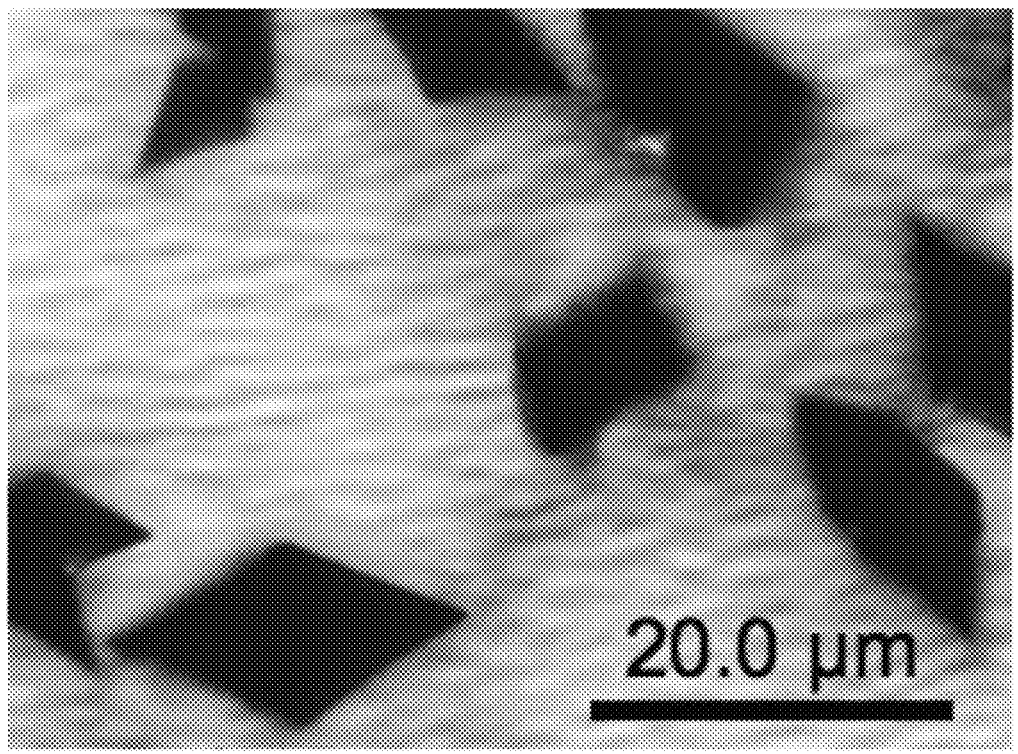

Freshly prepared and fully protonated clusters were dissolved in DMF with a concentration of 10.0 mg/mL. The vials were sealed with a septum, and Ar gas was passed through the vials to evaporate the solvent. Rhombus-shaped crystals were obtained in 1-3 days, as shown in FIGS. 10A-10B. The crystals were dark red in color when illuminated with transmitted light, although they were often too thick for light to pass through. The crystals were brittle and varied in size from less than a micron to several hundred microns in their longest dimension.

Single Crystal X-Ray Diffraction and Analysis

The single-crystal data were collected from a crystal of approximate dimensions of 80×70×50 µm³, which was mounted with a MiTeGen MicroLoop and cooled to 150 K for data collection. X-ray diffraction data were collected on a Bruker Apex Duo diffractometer (graphite-monochromated, CuKα=1.54178 Å), which was equipped with an Apex II CCD detector and an Oxford Cryostream 700 low temperature device. Data were integrated using SAINT. Corrections for absorption and decay were applied using SADABS. Data integration using a trigonal unit cell yielded a total of 140794 reflections to a maximum angle of θ=68.10° (0.83 Å resolution), of which 14088 were independent (average redundancy 9.994, completeness=97.0%, $R_{int}$=6.11%, $R_{sig}$=3.82%) and 10518 (74.66%) were greater than 20 σ(I).

The structure was solved and refined with the Bruker SHELXTL software package using the R3c space group, with Z=6 for the formula unit, $C_{210}H_{150}Ag_{44}Na_4O_{60}S_{30}$. All unique reflections were used in the refinement. The final anisotropic full-matrix least-squares refinement on $F^2$ with 471 variables converged at R1=5.20%, for the observed data, and wR2=18.34% for all data. The goodness-of-fit was 1.136. The largest peak in the final difference electron density synthesis was 1.028 e⁻/Å³ with an RMS deviation of 0.250 e⁻/Å³.

All eight crystallographically independent Ag atoms were obtained by direct methods, and all remaining non-hydrogen atoms were located with subsequent difference Fourier techniques. The Ag$_{44}$(SC$_6$H$_4$COOH)$_{30}$ core is located over the $\bar{3}$ bar with one Ag atom on the crystallographic 3-fold axis leading to Z' of ⅙ of the molecule. While the Ag—S core is ordered, all thiolate ligands are included as disordered over two positions.

Disordered atoms were refined with isotropic thermal displacement parameters. All Ag, S, and non-disordered C atoms were refined with anisotropic displacement parameters with the exception of C57 for which neither a disorder model nor a sensible anisotropic model could be found. Occupancies of the two sets of C and O atoms for each thiolate ligand were refined, but constrained to add up to 1, with Uiso fixed to the same value for all relevant atoms. At a later stage of the refinement, the occupancies were fixed to the approximate refined value (0.50 for all five ligands) and the atomic displacement parameters were refined. Hydrogen atoms were not included in the final refinement. 7 restraints (Flat, SADI) and 4 constraints (EADP) were used in the final refinements.

Neither the cation nor the solvent molecules could be identified from the X-ray structure data (highest residual electron density: 1.028 e$^-$/Å$^3$), however, the structure converged to R1=5.2%. PLATON was used to calculate the total accessible void volume and estimate the total electron count per unit cell. Void volume and electron calculations are based on a structure refinement that includes the hydrogen atoms. Based on this calculation, the total potential solvent accessible void volume is estimate to be ~50% of the cell volume, or 36,200 Å$^3$ with an electron count of 18,900 electrons/cell. This electron count has not been included in F(000), density, or molecular weight.

Structural Analysis of the Ag$_{44}$(p-MBA)$_{30}$$^{4-}$ Cluster

Figure 11:
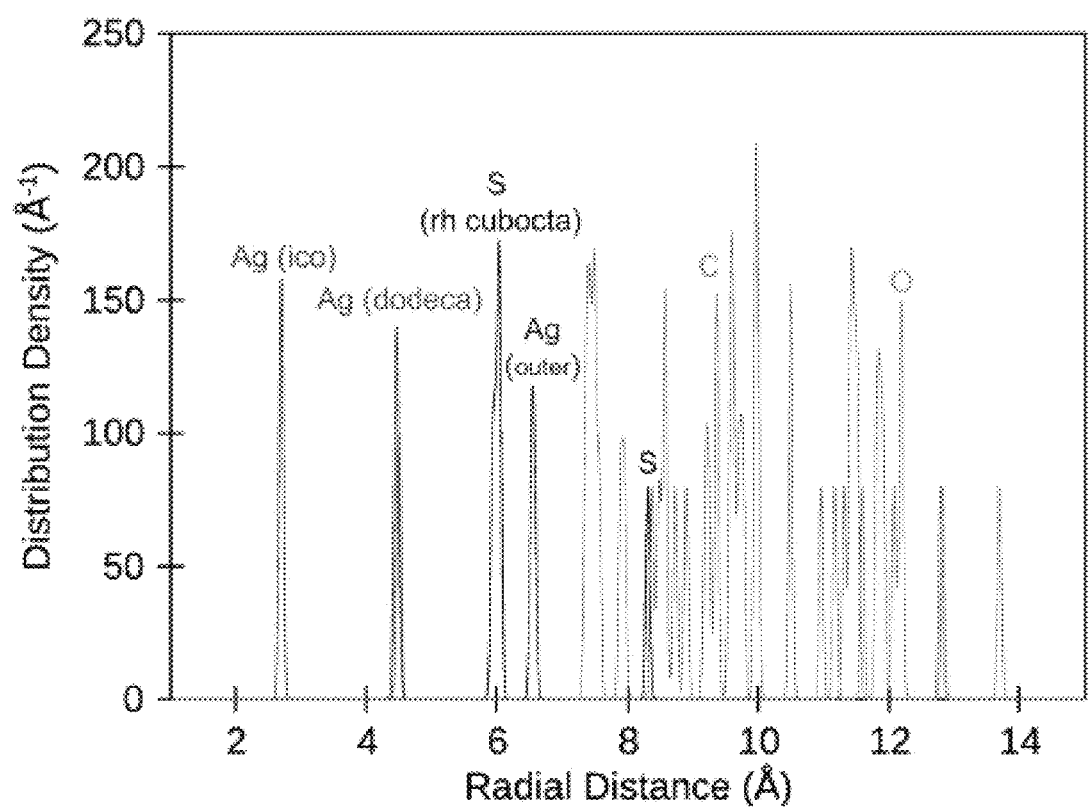
FIG. 11: Radial atomic distance distribution, with respect to the center of the x-ray-determined structure of the $Ag_{44}$ (p-MBA)$_{30}^{4-}$ cluster. The various atomic shells are distinguished by color and noted in the figure. The radial distances of the 6 outer sulfur atoms is given in black (centered about 8.2 Å). A Gaussian convolution with σ=0.03 Å was used.

Radial distances are displayed in Table 1, and interatomic distances are displayed in Table 2. Additionally, the radial atomic distance distribution is shown in FIG. 11, a summary of sample and crystal data for the Na$_4$Ag$_{44}$(p-MBA)$_{30}$ cluster is shown in Table 3 in FIG. 12, data collection and structure refinement for the M$_4$Ag$_{44}$(p-MBA)$_{30}$ cluster is displayed in Table 4 in FIG. 13, atomic coordinates and equivalent isotropic atomic displacement parameters are displayed in Table 5 in FIG. 14, bond lengths are displayed in Table 6 in FIG. 15, bond angles are displayed in Table 7 in FIG. 16, and anisotropic atomic displacement parameters are displayed in Table 8 in FIG. 17. All the information in these tables and figures was obtained by analyzing the X-ray-determined structure discussed above.

The hierarchical shell-by-shell buildup of the structure is displayed in FIGS. 1C-1F. The core (FIGS. 3C-3D) can be described as a 32-atom excavated dodecahedron in which 20 outer atoms lie at the vertices of a pentagonal dodecahedron, 12 inner atoms lie at the vertices of a regular icosahedrons, and there is no central atom. The core approximates icosahedral symmetry, I$_h$, the highest point-group symmetry. The average nearest-neighbor (nn) distance within the 12 Ag-atom inner-core icosahedrons (red in FIGS. 1C-1F) is 2.826±0.011 Å. The remaining outer 12 Ag atoms are distanced greater than 3.1 Å from the nearest (32 atom) core atoms, and each is triply coordinated to sulfur atoms via short (and strong) bonds. Each of the inner 12 Ag atoms has 10 nearest neighbors (5 on the icosahedrons itself and the other 5 on the surrounding 20-atom shell) in a locally D$_{5d}$ arrangement. The 20 Ag atoms of the pentagonal dodecahedron (PD, the core surface) have, each, six neighbors among the core atoms. These 20 atoms occupy two distinct environments, in groups of 12 and 8, the latter at the vertices of a cube, causing their positions to deviate slightly from the local icosahedral sphere-packing. It is the precise coordination environment of these groups of 12 and 8 that imparts reduced (cubic group) symmetry to the core, and these deviations may reflect their interaction with the p-MBA monolayer.

The inner 12 Ag atoms are located ~2.69±0.005 Å from the (vacant) center and have no bonding to sulfur. Those in the second shell, of radius 4.48 Å, bind either two sulfurs (the group of 12) or three sulfurs (group of 8). The 12 Ag atoms in the outer shell of radius 6.543±0.025 Å also bind three sulfurs. Among the 30 sulfur atom sites, 24 lie within a thin shell of radius 6.0±0.05 Å, and each is triply coordinated to silver atoms (FIG. 1F). The remaining six sulfurs are located 8.3 Å from the center, near the vertices of a regular octahedron, where the slight sideways deflections are attributed to the pyramidal configuration about the coordinating thiolate S-atom. Each of these six sulfurs bridges a pair of the outer 12 Ag sites, which in turn are each coordinated to two of the 24 sulfur sites. The seven atoms form a capping unit termed a "mount" (see FIG. 1H). Altogether, six such Ag$_2$S$_5$ mounts comprise the entire layer protecting the compact, quasi-spherical 32-Ag core. The distances separating the outer Ag atoms (the ones in the mounts) from the silver atoms on the surface of the 32-Ag atom cluster core are larger compared to the distances separating atoms in the 32-Ag core. Furthermore, the Ag—S bond distances between the outermost Ag atoms—that is, the atoms of the Ag$_2$S$_5$ mount, which are 3-fold coordinated to the sulfurs of the mount with one bonded at 2.48 Å (short and therefore strong) and two slightly longer, at 2.51±0.02 Å—are the shortest (and thus strongest) bonds in the complex. By comparison, for the group of 12 Ag atoms on the surface of the 32-atom core (colored dark green in FIGS. 1A-1H) that are 2-fold coordinated to sulfur, the Ag—S distance is 2.55 Å. Moreover, the remaining 8 atoms on the surface of the core (colored light green in FIGS. 1A-1H) are 3-fold coordinated to sulfur, having an Ag—S distance of 2.64 Å, correlating with weaker bonds. This geometric analysis, as well as the bond multiplicities, indicates significant separability of the core from the capping mount elements.

TABLE 1

Radial Distances*

|    | average (Å) | min-max (Å)   | stdev (Å) |
|----|-------------|---------------|-----------|
| Ag | 2.688       | 2.683-2.692   | 0.005     |
| A1 | 4.448       | 4.433-4.464   | 0.016     |
| A2 | 4.481       | 4.475.4.499   | 0.011     |
| A3 | 6.543       | 6.520-6.567   | 0.025     |
| S1 | 5.990       | 5.921-6.034   | 0.048     |
| S2 | 8.302       | 8.302-8.302   | 0.000     |
| C  | 9.404       | 7.349-12.781  | 1.414     |
| O  | 12.125      | 11.167-13.689 | 0.666     |

*Notation -- Ag: inner-core (hollow icosahedrons) Ag atoms (12) (red in FIGS. 1A-1H); A1: group of 12 Ag atoms occupying dodecahedral sites (dark green in FIGS. 1A-1H); A2: group of 8 Ag atoms (forming a cube) occupying dodecahedral sites (light green in FIGS. 1A-1H); A3: outer 12 Ag atoms (blue in FIGS. 1A-1H); S1: 24 inner-shell S atoms (forming a rhombicuboctahedron) (yellow in FIGS. 1A-1H); S2: 6 outer S atoms (forming an octahedron) (dark yellow in FIGS. 1A-1H); and C: carbon atoms.

TABLE 2

Interatomic Distances*

|                        | average (Å) | min-max (Å)  | stdev (Å) |
|------------------------|-------------|--------------|-----------|
| Ag—Ag                  | 2.826       | 2.813-2.843  | 0.011     |
| Ag-A1 and Ag-A2        | 2.841       | 2.813-2.868  | 0.019     |
| A1-A1, A1-A2, and A2-A2| 3.184       | 3.138-3.223  | 0.037     |

TABLE 2-continued

Interatomic Distances*

| | average (Å) | min-max (Å) | stdev (Å) |
|---|---|---|---|
| A3-A3 | 2.996 | 2.996-2.996 | 0.000 |
| S—S | 4.325 | 4.035-4.643 | 0.219 |
| S1-A3 | 2.511 | 2.485-2.528 | 0.017 |
| S1-A1 | 2.548 | 2.534-2.569 | 0.013 |
| S—C | 1.768 | 1.697-1.831 | 0.044 |

*Notation -- Ag: inner-core (hollow icosahedrons) Ag atoms (12) (red in FIGS. 1A-1H); A1: group of 12 Ag atoms occupying dodecahedral sites (dark green in FIGS. 1A-1H); A2: group of 8 Ag atoms (forming a cube) occupying dodecahedral sites (light green in FIGS. 1A-1H); A3: outer 12 Ag atoms (blue in FIGS. 1A-1H); S1: 24 inner-shell S atoms (forming a rhombicuboctahedron) (yellow in FIGS. 1A-1H); S2: 6 outer S atoms (forming an octahedron) (dark yellow in FIGS. 1A-1H); and C: carbon atoms.

Calculation of the Projected Density of States (PDOS)

Figure 6B:
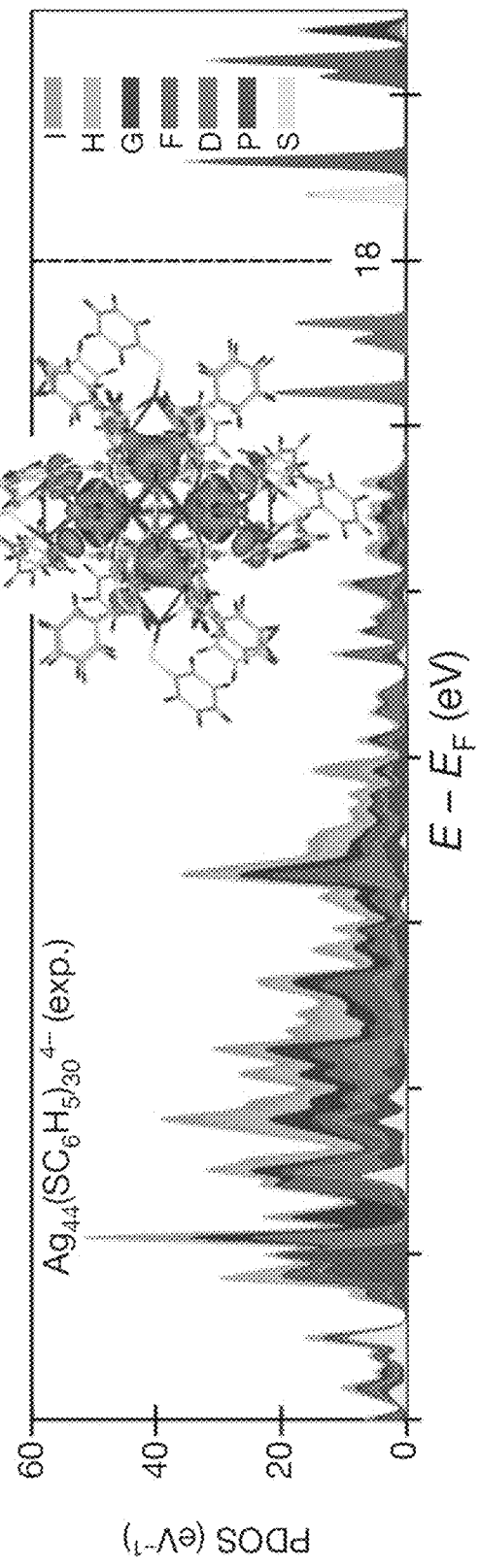

The projected local density of states (PDOS), depicted in FIGS. 6A-6C, was calculated from the Kohn-Sham (KS) orbitals $\psi_i(r+R_{cm})$, where $R_{cm}$ is the center of mass of the cluster (taken here as the origin, $R_{cm}=0$), using the following equations:

$$W_{i,l}(R_0) = \sum_{m=-l}^{l} \int_0^{R_0} r^2 \, dr |\varphi_{i,lm}(r)|^2, \quad \text{Equation 3}$$

and $$\varphi_{i,lm}(r) = \int d\Omega Y_{lm}(\Omega)\psi_i(r) \quad \text{Equation 4}$$

Here, $Y_{lm}$ is the spherical harmonic function with angular momentum number l and magnetic quantum number m, and the angular momenta up to l=6 (I symmetry) are included; the symmetries associated with the angular momentum numbers l=0, 1, 2, 3, 4, 5, and 6 are denoted as S, P, D, F, G, H, and I, respectively. The integration was taken in a sphere of radius $R_0$, chosen as follows: for $Ag_{44}(SC_6H_5)_{30}^{4-}$, $R_0=5.21$ Å; for $Ag_{32}^{14+}$ and $Ag_{20}^{2+}$, $R_0=12.0$ Å.

Certain embodiments of the compounds and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A compound comprising the formula $M_4Ag_{44}(SR)_{30}$ wherein:

M is a metal selected from the group consisting of Cs, Na, K, Li, Fr, and Rb; and SR is a mercaptophenyl ligand; and salts and isomers thereof.

2. The compound of claim 1, wherein the mercaptophenyl ligand is selected from the group consisting of p-mercaptobenzoic acid, p-mercaptophenyl alcohol, and 4-mercaptophenol.

3. The compound of claim 1, further comprising coordinating molecules selected from the group consisting of: deprotonated methanol ions, deprotonated ethanol ions, hydroxide ions, citrate, acetate, DMSO, DMF, pyridine, ammonia, acetone, acetonitrile, ethers, phosphines, and combinations thereof.

4. The compound of claim 3, wherein the compound has a core comprising coordination sites, and the coordinating molecules stabilize the compound by binding to the coordination sites.

5. The compound of claim 4, wherein one or more of the coordinating molecules is substituted by one or more of a pharmaceutical agent, a fluorophore, or a carbohydrate, covalently bonded through a sulfur linkage at a coordination site.

6. The compound of claim 1, wherein the compound comprises a $Ag_{32}$ core and a protecting layer of $Ag_2S_5$ capping structures.

7. A silver cluster molecule comprising: a 32-silver-atom dodecahedral core consisting of a 12-silver-atom icosahedron encapsulated by a 20-silver-atom dodecahedron; and 30 coordinating ligands.

8. The silver cluster molecule of claim 7, wherein the coordinating ligands comprise p-MBA.

9. The silver cluster molecule of claim 7, wherein the dodecahedral core comprises icosahedral symmetry.

10. The silver cluster molecule of claim 7, wherein four sulfur atoms connect the mounts to the core.

11. The silver cluster molecule of claim 7, wherein the silver atoms in the icosahedral core do not contact the coordinating ligands.

12. The silver cluster molecule of claim 7, wherein each coordinating ligand comprises atoms defining a rhombicuboctahedron capped with six $Ag_2S$ units.

13. A method of making silver nanoparticles, the method comprising:

preparing a Ag(I)—SR precursor compound;

reducing the Ag(I)—SR precursor compound to grow silver nanoparticles; and removing by-products to isolate the silver nanoparticles;

wherein SR is a mercaptophenyl ligand.

14. The method of claim 13, wherein preparing the Ag(I)—SR precursor compound comprises adding a solvent to a mixture of silver nitrate and a mercaptophenyl ligand.

15. The method of claim 14, further comprising adding a base to the mixture of silver nitrate and a mercaptophenyl ligand.

16. The method of claim 13, further comprising adjusting the pH to about 9 to solubilize the Ag(I)—SR precursor.

17. The method of claim 13, further comprising adjusting the pH to about 12 to stabilize the silver nanoparticles.

18. The method of claim 13, wherein the reducing comprises adding a reducing agent to the Ag(I)—SR precursor compound, wherein the reducing agent is selected from the group consisting of: $NaBH_4$, $LiBH_4$, $KBH_4$, $Al(BH_4)_3$, and combinations thereof.

19. The method of claim 13, wherein the by-products are removed by precipitating the silver nanoparticles, and collecting the precipitated silver nanoparticles.

20. The method of claim 19, wherein the nanoparticles are precipitated by the addition of a non-solvent selected from the group consisting of: methanol, DMF, toluene, and combinations thereof.

* * * * *